(12) United States Patent
Vogt et al.

(10) Patent No.: US 12,011,571 B2
(45) Date of Patent: Jun. 18, 2024

(54) DEVICE AND METHOD FOR MIXING LIQUIDS

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 478 days.

(21) Appl. No.: 17/324,702

(22) Filed: May 19, 2021

(65) Prior Publication Data

US 2021/0361872 A1 Nov. 25, 2021

(30) Foreign Application Priority Data

May 19, 2020 (EP) .................................... 20175365

(51) Int. Cl.
*A61M 5/28* (2006.01)
*A61B 17/00* (2006.01)
*A61M 5/19* (2006.01)

(52) U.S. Cl.
CPC ....... *A61M 5/284* (2013.01); *A61B 17/00491* (2013.01); *A61M 5/19* (2013.01); *A61B 2017/00495* (2013.01)

(58) Field of Classification Search
CPC ... A61M 5/284; A61M 5/19; A61B 17/00491; A61B 2017/00495; B01F 2101/2202;
(Continued)

(56) References Cited

U.S. PATENT DOCUMENTS 3,223,083 A 12/1965 Milton
3,861,652 A 1/1975 Clark et al.
(Continued)

FOREIGN PATENT DOCUMENTS

DE 1491877 5/1969
DE 2638086 1/1977
(Continued)

*Primary Examiner* — Bob Zadeh
(74) *Attorney, Agent, or Firm* — Dicke, Billig & Czaja, PLLC

(57) ABSTRACT

One aspect relates to a device for mixing two liquids including a tube having an open end, a main line connected to the tube in a liquid-permeable manner, a rubber-elastic body delimiting a line wall of the main line, at least one secondary line in the rubber-elastic body, wherein the at least one secondary line extends from at least one secondary opening up to the main line and opens via at least one mouth into the main line, a main connection for introducing a first liquid into the main line, at least one feed line for introducing a second liquid into the at least one secondary line, which is connected to the at least one secondary opening in a liquid-permeable manner. The at least one secondary line is closed in the rubber-elastic body without the action of a force and is hydraulically openable by a pressure being exerted on a second liquid fed to the at least one secondary line by an elastic deformation of the at least one rubber-elastic body. The open at least one secondary line closes without a pressure being exerted on the supplied second liquid by the restoring force of the elastically deformed rubber-elastic body.

23 Claims, 24 Drawing Sheets

(58) Field of Classification Search
CPC .. B01F 25/27; B01F 25/314; B01F 25/31423; B01F 25/3143; B01F 33/50112; B01F 23/451
See application file for complete search history.

(56) References Cited

U.S. PATENT DOCUMENTS

| | | | |
|---|---|---|---|
| 4,039,369 A | | 8/1977 | Versteege |
| 4,109,653 A | | 8/1978 | Kozam |
| 4,359,049 A | | 11/1982 | Redl et al. |
| 4,655,747 A | * | 4/1987 | Allen, Jr. ............... A61M 5/19 604/191 |
| 5,385,606 A | | 1/1995 | Kowanko |
| 6,045,570 A | * | 4/2000 | Epstein ............ A61B 17/0057 606/214 |
| 2003/0032937 A1 | * | 2/2003 | Griego ............ A61M 25/0026 514/3.3 |
| 2009/0038701 A1 | * | 2/2009 | Delmotte .......... B01F 33/50112 137/896 |
| 2012/0104030 A1 | * | 5/2012 | Springhorn ....... B05C 17/00553 222/137 |
| 2013/0131632 A1 | * | 5/2013 | Mudd ................. A61M 5/1407 604/506 |
| 2013/0317423 A1 | * | 11/2013 | Kane ................ B05C 17/00593 604/82 |
| 2020/0276546 A1 | | 9/2020 | Katzarov et al. |
| 2021/0361872 A1 | * | 11/2021 | Vogt ..................... A61M 5/284 |

FOREIGN PATENT DOCUMENTS

| | | |
|---|---|---|
| DE | 2648086 | 9/1977 |
| EP | 0037393 | 10/1981 |
| EP | 0650512 | 5/1995 |
| JP | 2003305351 | * 10/2003 |
| TW | M378779 | 4/2010 |
| WO | 2014/090507 | 6/2014 |
| WO | 2019/052838 | 3/2019 |

* cited by examiner

DEVICE AND METHOD FOR MIXING LIQUIDS

CROSS-REFERENCE TO RELATED APPLICATIONS

This Utility patent application claims priority to European Application No. 20175365.4, filed on May 19, 2020, which is incorporated herein by reference.

TECHNICAL FIELD

One aspect relates to a device for mixing small volumes of two liquids, in particular two low-viscosity liquids. One aspect also relates to a method for producing a liquid mixture from two liquids by using such a device.

One aspect is in particular a device for mixing small volumes of thin two-component adhesives, especially soft tissue adhesives. The device is intended for mixing thin adhesive components which are stored in two-component cartridges. The two-component cartridge can be part of the device according to one embodiment.

BACKGROUND

Soft tissue adhesives have long been known in medicine. Cyanoarcylate adhesives are frequently used for topical applications. An example of this is an adhesive according to U.S. Pat. No. 3,223,083 A. For adhesive bonding of internal organs, two-component adhesives have proved successful which are based on aqueous protein solutions which are crosslinked with aqueous dialdehyde solutions. A widely used adhesive is based on human serum albumin and glutardialdehyde, as described, for example, in EP 0 650 512 B1. This adhesive consists of two very thin components which are usually mixed with the aid of a static mixer. The liquid starting components of this adhesive react with one another within a few seconds, approximately 30 to 45 seconds, to form a rubber-elastic, yellowish to orange solid. This means that if bonding has to be interrupted for medical reasons, the adhesive hardens within the static mixer. The cured adhesive cannot subsequently be pressed out of the static mixer. The adhesive package must be discarded. Therefore, a disadvantage of this is that a new two-component cartridge has to be used after each interruption in the adhesion process. Mixing the liquids in a mixing beaker is likewise unfavorable because of hygienic requirements and the small amount required.

Mixing systems in which both liquid components flow into one another have been proposed for mixing two liquid components; see, for example, documents DE 1 491 877 A1, EP 0 037 393 A1 and U.S. Pat. No. 4,109,653 A.

Static mixers have been generally known for decades. Exemplary mixers are known from the publications DE 26 48 086 A1, TW M378779 U1, U.S. Pat. No. 3,861,652 A and WO 2019/052838 A2.

For these and other reasons there is a need for the present embodiment.

SUMMARY

An object of one embodiment is thus to overcome the disadvantages of the prior art. In particular, it is an object of one embodiment to develop a cost-effective and easy-to-use device for producing a fast-curing liquid mixture from two liquids which can also be used further for mixing, producing and discharging the liquid mixture from the two liquids even after the mixing process has been interrupted and after the liquid mixture has cured in the device. The device is intended to be further usable without modification measures in order to produce and dispense the liquid mixture. The construction should be cost-effective and simple to use. In order to ensure medical use under hygienic conditions, the device should be able to be disposed of cost-effectively and hygienically after use. For this purpose, it is advantageous if the device can be incinerated as completely as possible. It should be possible for the user to handle the device as easily as possible.

It is also an object of one embodiment to develop a device for mixing very small volumes of reactive thin liquids and, in particular, thin two-component soft tissue adhesives. Volumes in the range of a few microliters should be able to be mixed. The mixer of the device is to be designed in such a way that only very small volumes of the liquids or the adhesive starting components are contained in the cavity of the mixer. The mixed liquid components are not to be allowed to flow back into the incoming liquid components.

Objects of one embodiment are achieved by a device for mixing small volumes of a first liquid and a second liquid, the device including a tube having a line cross-sectional area of at most 2 mm$^2$ or having an inner diameter of at most 1.5 mm, wherein the tube has an open end, a main line which is connected to the tube in a liquid-permeable manner on the side opposite the open end, at least one rubber-elastic body which delimits a line wall of the main line at least in some regions or which delimits the entire main line, at least one secondary line, which is formed in the at least one rubber-elastic body, wherein the at least one secondary line extends from at least one secondary opening in the surface of the at least one rubber-elastic body up to the main line and opens into the main line via at least one mouth in the at least one rubber-elastic body, a main connection for introducing a first liquid into the main line, at least one feed line for introducing a second liquid into the at least one secondary line, wherein the at least one feed line is connected to the at least one secondary opening in a liquid-permeable manner, wherein the at least one secondary line is closed in the at least one rubber-elastic body without the action of a force and is hydraulically openable by a pressure being exerted on a second liquid, supplied to the at least one secondary line, by an elastic deformation of the at least one rubber-elastic body, and wherein the open at least one secondary line closes without a pressure being exerted on the supplied second liquid by the restoring force of the elastically deformed at least one rubber-elastic body.

BRIEF DESCRIPTION OF THE DRAWINGS

Further exemplary embodiments are explained below with reference to twenty-two schematically depicted figures, but without thereby restricting the invention. Therein.

DETAILED DESCRIPTION

Figure 1:
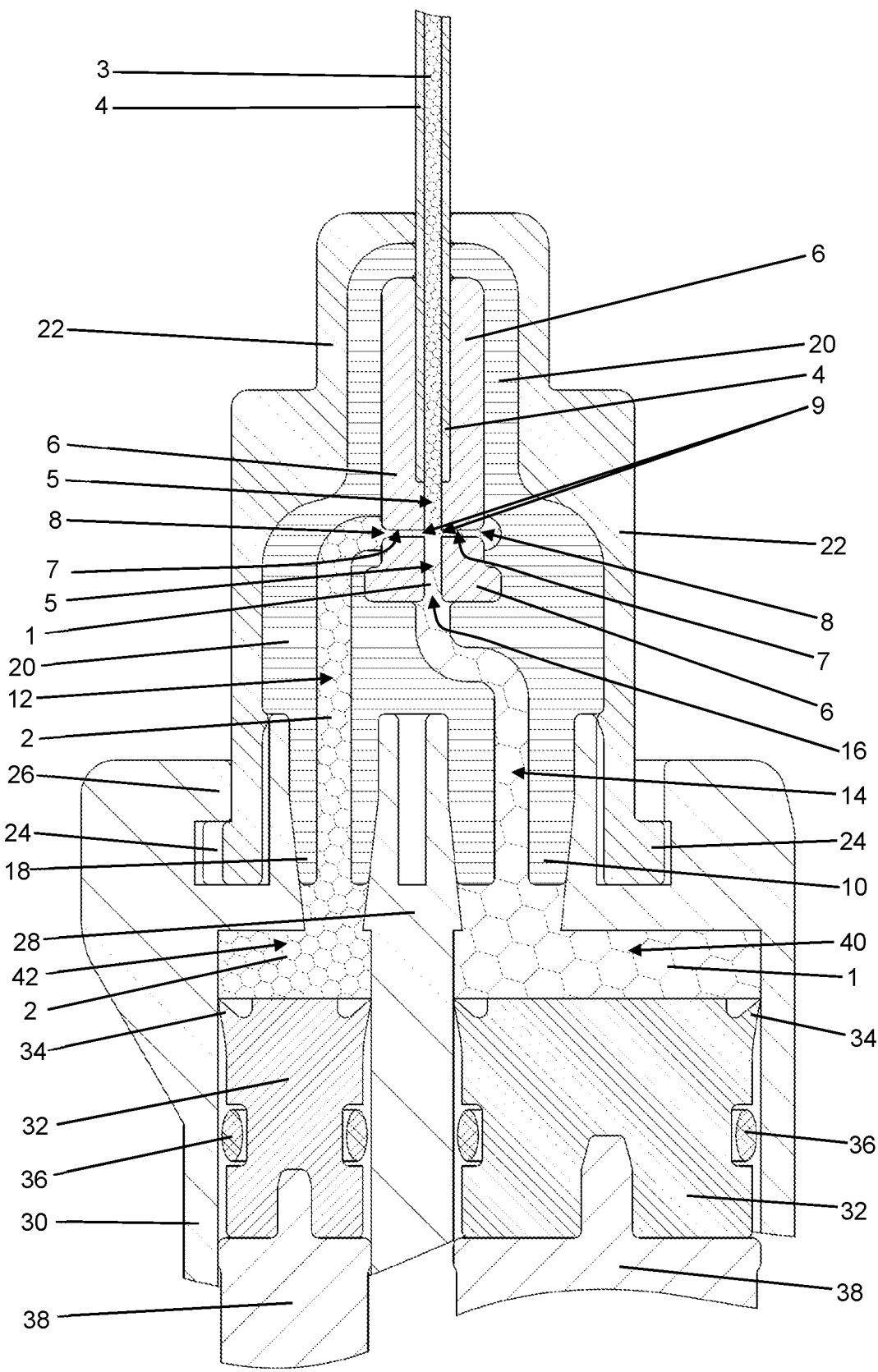
FIG. 1: illustrates a schematic cross-sectional view of a detail enlargement of an exemplary device according to one embodiment for mixing liquids during a mixing process.
Figure 2:
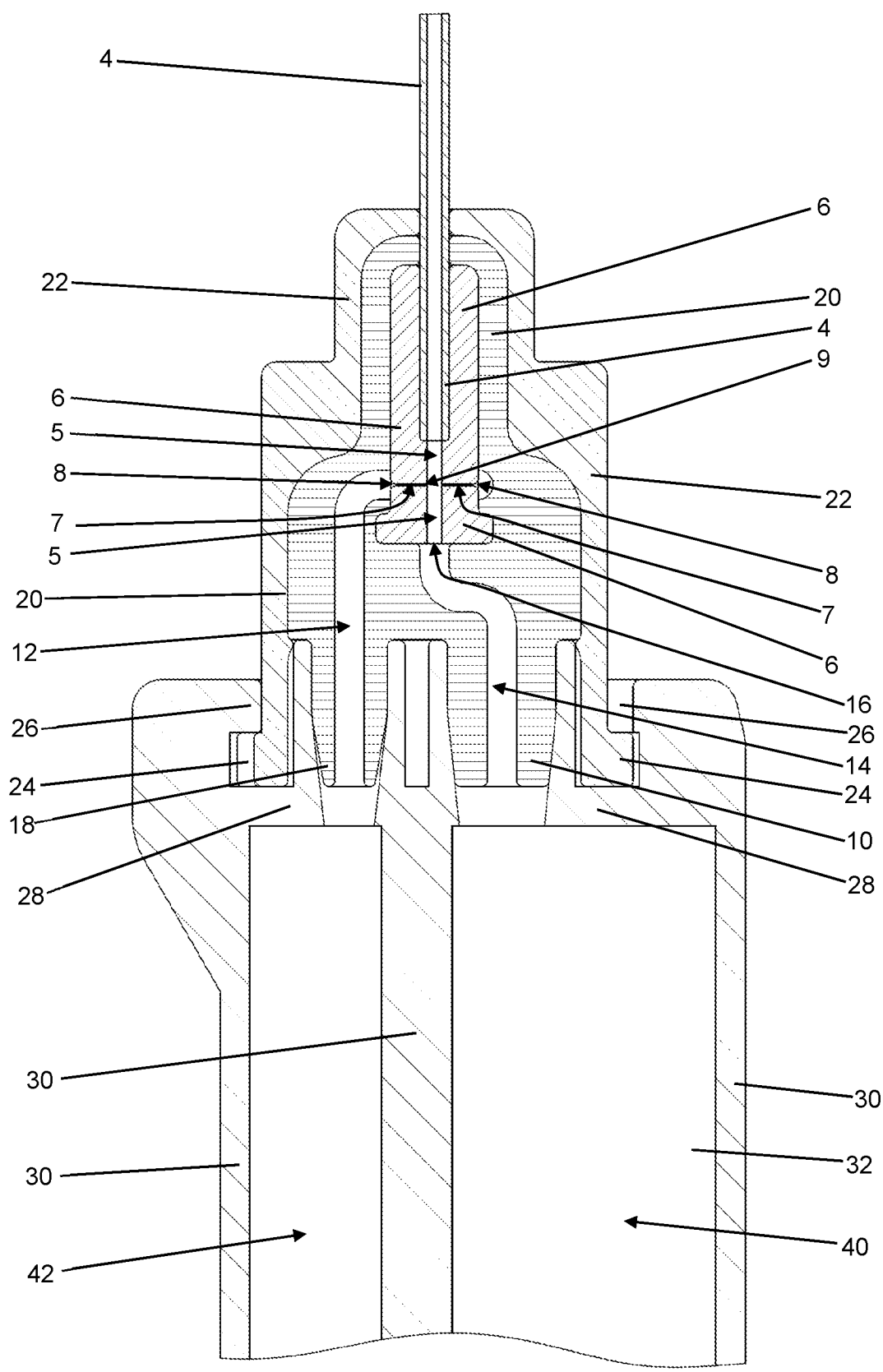
FIG. 2: illustrates a schematic cross-sectional view of a detail enlargement of the device according to FIG. 1 with closed secondary lines.
Figure 3:
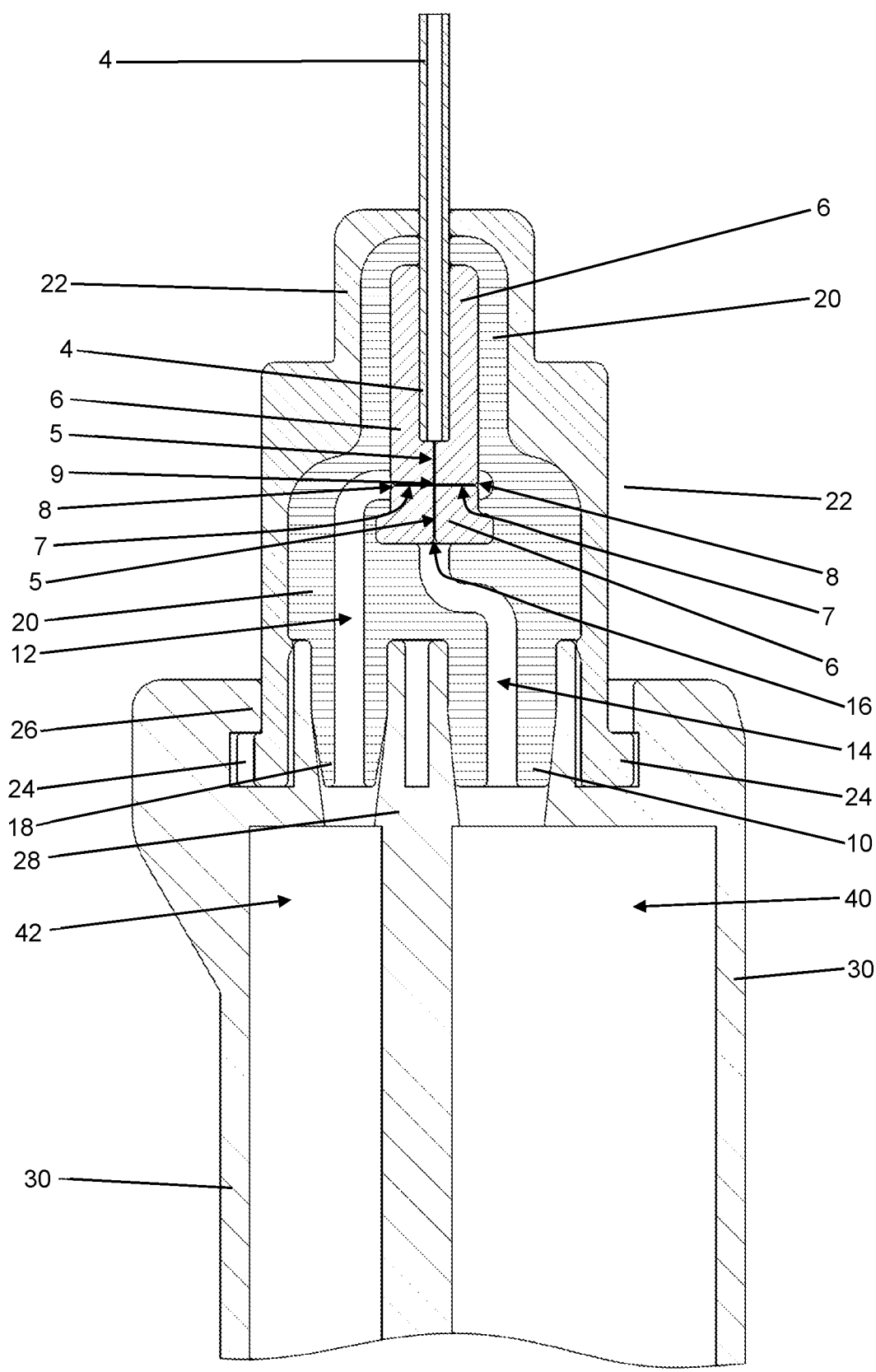
FIG. 3: illustrates a schematic cross-sectional view of a detail enlargement of the device of FIG. 1 with closed main and secondary lines.
Figure 4:
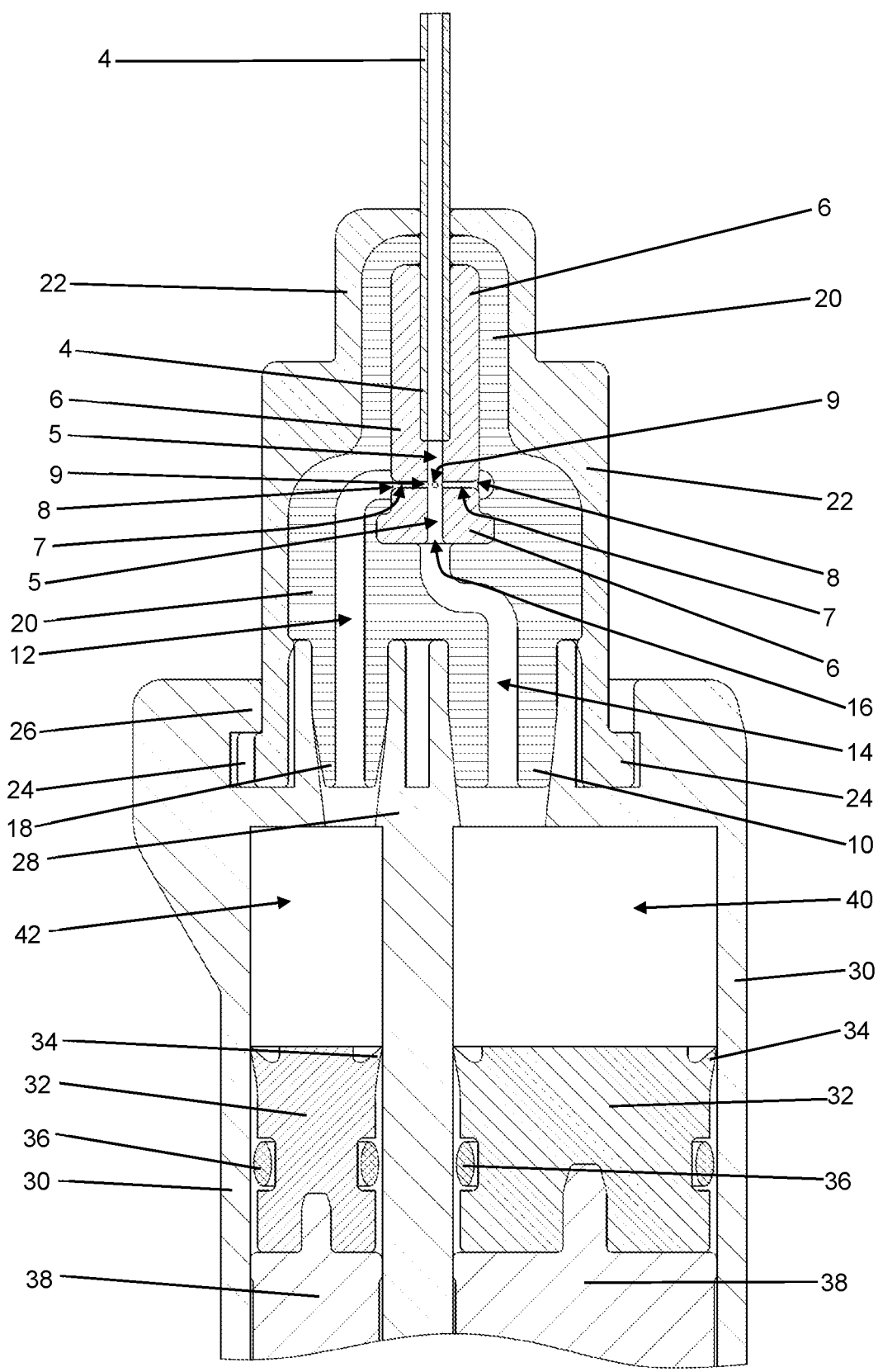
FIG. 4: illustrates a schematic cross-sectional view of a detail enlargement of the device of FIG. 1 with opened main and secondary lines.
Figure 5:
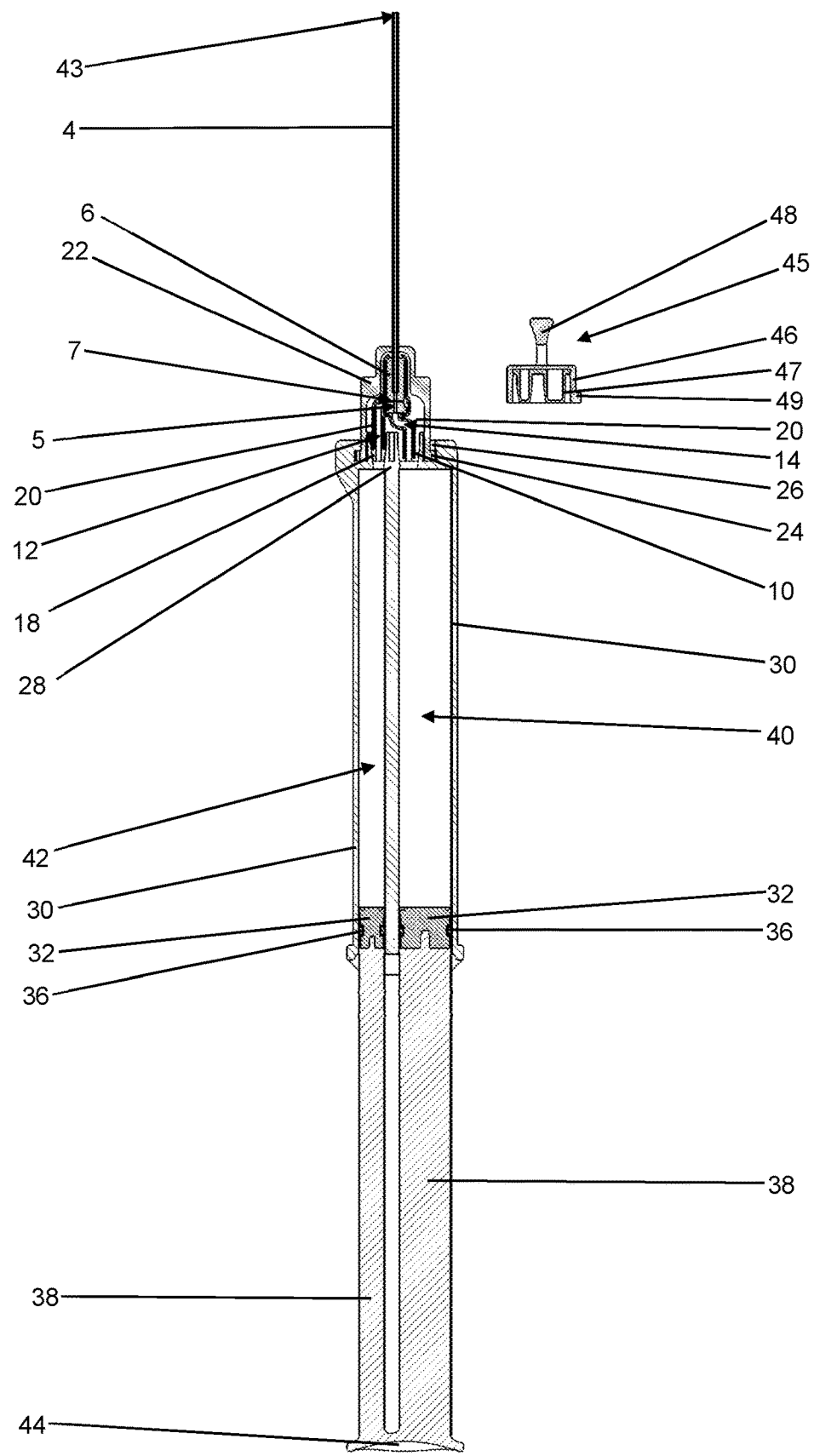
FIG. 5: illustrates a schematic cross-sectional view of the entire device prior to mixing.
Figure 6:
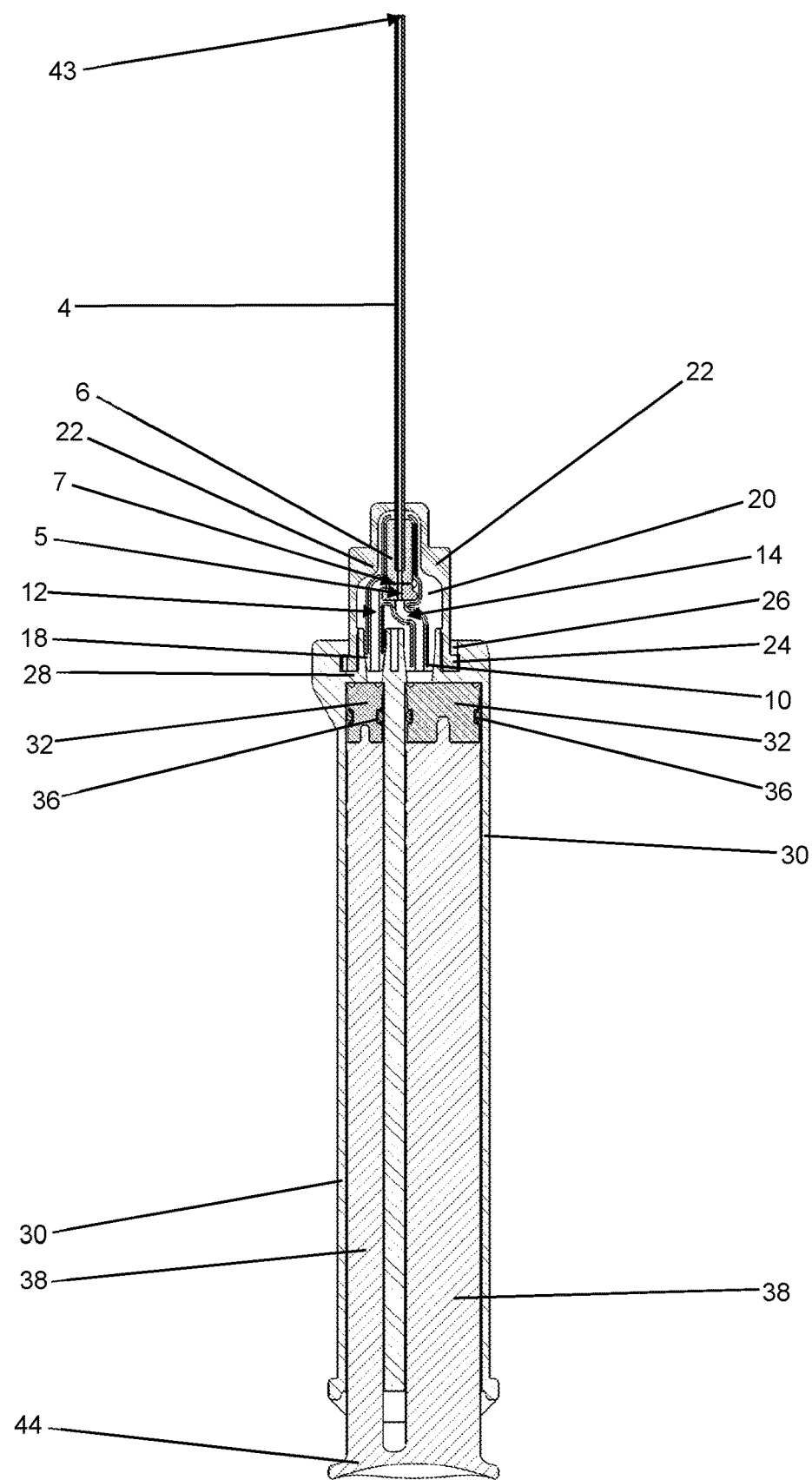
FIG. 6: illustrates a schematic cross-sectional view of the entire device after mixing.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

In the figures, the same reference signs are also used for different exemplary embodiments since the exemplary embodiments differ only slightly and, at the same time, the comparability of the exemplary embodiments is improved.

The at least one rubber-elastic body is in one embodiment at least one rubber-elastic solid body, in which the at least one secondary line is contained and particularly in one embodiment the main line is also contained.

When the at least one secondary line is hydraulically opened, a force acting via the second liquid is passed on and the inner diameter and thus the line cross section of the at least one secondary line are opened and widened. By the widening of the at least one secondary line, the second liquid can flow through the at least one secondary line into the main line.

The at least one mouth of the at least one secondary line into the main line can be constructed with a lip valve. The lip valve or the lip valves are then the rubber-elastic body, and the at least one secondary line is the at least one passage through the at least one lip valve. This is a special embodiment with a very compact rubber-elastic body. However, a more voluminous rubber-elastic body is in one embodiment used in which the secondary lines in the rubber-elastic body are at least 1 mm long.

The main connection is in one embodiment connected to the main line on the side opposite the tube.

The device is in one embodiment a medical device for producing a medically usable liquid mixture, in particular for producing a medical tissue adhesive.

The at least one secondary line being formed in the at least one rubber-elastic body means that the at least one rubber-elastic body forms the walls of the at least one secondary line. The same applies similarly, if necessary, to the main line if the latter is likewise formed in the at least one rubber-elastic body.

The first liquid and the second liquid are in one embodiment of low viscosity. Particular in one embodiment, low-viscosity liquids are to be understood as those liquids which at room temperature have a viscosity of at most 10 mPa·s (0.01 Pa·s), very particularly in one embodiment have a viscosity of at most 1 mPa·s (0.001 Pa·s). For this purpose, the viscosity can be measured, for example, using a viscometer according to DIN EN ISO 2431:2011.

The mixer of the device is the region of the main line in which the second liquid can be injected into the main line via the at least one mouth.

The at least one rubber-elastic body can be a cylindrical sleeve, wherein the main line is a passage extending axially through the sleeve and the at least one secondary line extends from a lateral surface of the cylindrical sleeve up to the main line. Provision can also be made for the at least one rubber-elastic body to be at least one cylindrical sleeve, wherein each at least one secondary line extends axially through the at least one cylindrical sleeve in each case, and one of the main surfaces of the at least one cylindrical sleeve in each case forms a wall of the main line, wherein in one embodiment the main surfaces of a plurality of cylindrical sleeves are arranged opposite one another and/or at the same height of the main line.

The tube may consist of a plastic, in one embodiment a plastic which does not chemically bond to the liquid mixture and particularly in one embodiment also does not chemically bond with the first liquid or the second liquid.

The inner diameter of a line or of the tube is to be understood as assuming that the line or the tube has a circular or approximately circular internal line cross-sectional area in the interior.

The cross-sectional area of a line or of a line cross-sectional area is to be understood as the open area perpendicular to the direction of flow in the line which is available for conducting the liquid in the line.

The at least one mouth is in one embodiment closed in the pressure-free state (i.e. without an increased pressure of the second liquid acting on the inner walls of the secondary line).

The at least one mouth can be at least one injection opening.

The at least one rubber-elastic body can consist of all known biocompatible elastomers. Typical suitable elastomers are EPDM, silicone rubber, natural rubber, butadiene-acrylonitrile rubber and synthetic polyisoprene rubber.

Provision can be made for the at least one rubber-elastic body to be a single rubber-elastic body in which the main line and the at least one secondary line are formed.

In this way, the main line and the at least one secondary line and the connection can be produced in a rubber-elastic solid body, for example by drilling through and/or piercing the rubber-elastic solid body. As a result, the construction is simplified, compact and cost-effective.

According to one embodiment, the tube is inserted into the main line, wherein in one embodiment the tube does not cover the at least one mouth of the at least one secondary line into the main line.

As a result, the tube can be easily connected to the main line in a liquid-tight and pressure-tight manner. Theoretically, a lateral passage or a plurality of lateral passages can also be present in the wall of the tube, which passages are pushed over the at least one mouth such that the at least one mouth opens into the main line or the tube through the at least one passage in the wall of the tube.

According to one embodiment, it is also possible for the rubber-elastic body to be covered by a casing at least in the region of the secondary opening, wherein in one embodiment the casing coaxially surrounds the rubber-elastic body, and the main line runs along or parallel to the axis of the casing in the rubber-elastic body, wherein particularly in one embodiment the at least one feed line is designed as at least one liquid-permeable intermediate space between the casing and the rubber-elastic body.

As a result, a particularly simple construction of the device is achieved. According to one embodiment, the casing can be designed as a circumferential shell.

Furthermore, provision can be made for the tube to be connected to the main line in a liquid-tight and pressure-tight manner, for the main connection to be connected to the main line in a liquid-tight and in one embodiment pressure-tight manner, and for the second feed line to be connected to the at least one secondary opening in a liquid-tight and in one embodiment also pressure-tight manner.

This ensures that, when the device is used, neither the first liquid nor the second liquid for producing the liquid mixture nor the liquid mixture can escape from the device apart from via the tube.

Provision can also be made for the inner diameter of the main line or the inner diameter of the main line in an expanded state to have the same internal cross section as the tube, and/or for the tube to delimit a straight cylindrical line in its interior, wherein in one embodiment no projections or depressions are in the tube, particularly in one embodiment the tube is smooth in its interior.

As a result, it can be ensured that a plug formed by solidifying or curing the liquid mixture can be expelled easily from the cylindrical line or from the transition of the main line to the tube so that a new liquid mixture can be subsequently applied. This ensures that, after an interruption with the same device, a new liquid mixture of the first liquid and the second liquid can be produced and discharged.

Provision can also be made for the at least one mouth to be flush with the inner wall of the main line and/or for the tube to be flush with the main line or for the tube to be flush with the main line in the expanded state.

This prevents a solid plug from forming in the main line when the discharge of the liquid mixture of first liquid and second liquid is interrupted, said plug being firmly and non-detachably anchored in the main line via undercuts which are caused by the at least one mouth. This ensures that, after an interruption in the discharge of the liquid mixture of the liquids with the same device, a new liquid mixture can be produced and discharged. The flush condition particularly concerns the at least one mouth in the closed state. In the opened state, the at least one mouth can theoretically also project or be recessed slightly into the line.

It is also possible for the at least one secondary line to be at least 1 mm long, in one embodiment at least 5 mm long, and/or for the main line to be at least 3 mm long, in one embodiment at least 5 mm long.

As a result, the at least one secondary line can be completely closed and an undesired return flow of liquid mixture through the at least one secondary line can be prevented. Since there is usually no counterpressure on the open end of the tube, while the second liquid has to be conducted with a pressure through the at least one secondary line, the second liquid contained in the at least one secondary line is pressed into the main line in the direction of the tube during a contraction (i.e. an elastic closing) of the at least one secondary line because the decreasing pressure in the at least one secondary line is reduced only in the direction of the pressure-free, open end of the tube.

As a result of the minimum length of the main line, unmixed liquid always remains in the main line when the pressing-out and mixing process has been interrupted. As a result, when the first liquid and the second liquid are pressed out again, the first liquid can push the adhesive, cured in the region of the at least one mouth, out of the main line and out of the adjoining cavity of the tube so that the cured liquid mixture or the cured adhesive in the form of a cylinder exits or can be pressed out of the open end of the tube.

Furthermore, provision can be made for the main line to be connected via the main connection to a main reservoir containing the first liquid and for the at least one feed line to be connected to a secondary reservoir containing the second liquid, wherein in one embodiment a first delivery plunger is arranged in the main reservoir, by means of which first delivery plunger the first liquid is pressable from the main reservoir into the main line, and a second delivery plunger is arranged in the secondary reservoir, by means of which second delivery plunger the second liquid is pressable from the secondary reservoir into the at least one feed line, wherein particularly in one embodiment the first delivery plunger and the second delivery plunger are firmly connected to one another.

As a result, the device can be used directly for producing the liquid mixture from the first liquid and the second liquid, without these having to be fed into the device beforehand.

The pressure for opening the at least one secondary line is then transmitted via the second liquid. The pressure on the second liquid can be generated by using the second delivery plunger.

Furthermore, provision can be made for the first liquid and the second liquid to be starting components of a medical tissue adhesive and for the device to be a device for producing a medical tissue adhesive.

The device is particularly suitable and usable for medical applications.

In one embodiment, provision can be made for the tube to have a line cross-sectional area of at most 1 mm$^2$ or an inner diameter of at most 1 mm, in one embodiment of at most 0.5 mm.

As a result, very small volume flows of the liquid mixture can be produced, as are used in the medical field for producing medical tissue adhesives.

It is also possible for the at least one mouth or the at least one secondary line in the opened state to have a diameter of at most 0.5 mm, in one embodiment a diameter of at most 0.3 mm.

This means that the at least one secondary line or the at least one mouth cannot be widened beyond the stated diameters with the aid of the device. This ensures that only a small volume flow of the second liquid of the first liquid flowing through the main line can be admixed by the at least one secondary line.

According to a development of one embodiment, provision can be made for the at least one secondary line to be at least two secondary lines and for the at least one mouth to be at least two mouths, wherein in one embodiment the at least two mouths are arranged on opposite sides of the main line, such that the second liquid injected into the main line through the at least two mouths directly meets in the main line.

This achieves better mixing of the second liquid injected through the at least two secondary lines with the first liquid conducted in the main line as a result.

Provision can furthermore be made for the main line and the at least one feed line to be connected or connectable to a two-component cartridge, wherein particularly in one embodiment the main line is connected or connectable via the main connection to a first chamber of the two-component cartridge, and the at least one feed line is connected or connectable to a second chamber of the two-component cartridge, wherein particularly in one embodiment the first liquid is contained as the first starting component in the first cartridge and the second liquid is contained as a second starting component in the second cartridge.

As a result, the device can be used directly for mixing the liquid mixture.

In one embodiment, provision can also be made for the main line to be formed in the at least one rubber-elastic body or be formed in a further rubber-elastic body, wherein the main line is closed in the at least one rubber-elastic body or in the further rubber-elastic body without the action of a force and is hydraulically openable by a pressure being exerted on the first liquid supplied to the main line by elastic deformation of the at least one rubber-elastic body or of the further rubber-elastic body, and wherein the open main line closes without a pressure being exerted on the supplied first liquid by the restoring force of the elastically deformed at least one rubber-elastic body.

As a result, curing of the liquid mixture in the rubber-elastic body can be avoided since the liquid mixture is pressed out of the main line into the tube with a sufficient reduction in the pressing-out pressure on the first liquid because the tube is open at its front side, while on the opposite side a counterpressure is present through the first liquid and the main line has to empty in the direction of the open tube end due to the contraction of the main line on account of the elastically deformed wall of the main line.

Furthermore, provision can be made for the at least one mouth into the at least one rubber-elastic body to be funnel-shaped and provide an opening into the at least one rubber-elastic body, in one embodiment even when no pressure acts on the at least one rubber-elastic body.

This ensures that the pressure of the second liquid can propagate into the at least one funnel-shaped opening and thus the at least one secondary line can be widened by the application of pressure. The funnel-shaped at least one mouth thus helps the second liquid to be able to penetrate well into the at least one secondary line from the at least one feed line in order to open said secondary line hydraulically there with the aid of a pressure on the second liquid.

If the main line is likewise formed at least in some regions in the at least one rubber-elastic body, it is also possible for the one main mouth of the main line into the rubber-elastic body to be funnel-shaped and to provide an opening into the at least one rubber-elastic body, in one embodiment even if there is no pressure acting on the at least one rubber-elastic body. The (closable or closed) main line can then also be easily opened in a manner similar to the at least one secondary line.

The objects of one embodiment are also achieved by a method for producing a mixture of two liquids, the method including the following chronological steps:

A) providing a two-component cartridge having a main reservoir, in which a first liquid is contained, and a secondary reservoir, in which a second liquid is contained;

B) pressing out the first liquid from the main reservoir into a main line and pressing out the second liquid from the secondary reservoir into at least two closed secondary lines, wherein the at least two secondary lines are formed in at least one rubber-elastic body;

C) opening the at least two secondary lines by elastic deformation of the at least one rubber-elastic body on account of a force exerted by the second liquid and transmitted hydraulically to the walls of the at least one secondary line;

D) injecting the second liquid into the first liquid in the main line through a plurality of mutually opposite mouths of the open at least two secondary lines into the main line and thereby mixing the first liquid with the second liquid, wherein the flows of the injected second liquid meet in the main line and, as a result, the mixing of the first liquid with the second liquid is promoted; and E) pressing out the liquid mixture through a tube connected to the main line.

A medical tissue adhesive is in one embodiment produced using the method.

The method is used only for producing the liquid mixture or the medical tissue adhesive. A medical application with a patient does not take place within the method.

The method does not contain any method steps excluded from the patent for medically treating a human or animal body. Such steps are optionally carried out following the method according to one embodiment.

Provision can be made for the method to be carried out using a device according to one embodiment, wherein in one embodiment the main reservoir is connected to the main connection and the main line in a liquid-permeable and pressure-tight manner, and the secondary reservoir is connected to the at least one feed line and the at least two secondary lines in a liquid-permeable and pressure-tight manner, or after step A) and before step B) a step A2) takes place: A2) connecting the device according to one embodiment or the remaining device to the two-component cartridge, wherein the main reservoir is connected to the main connection and the main line in a liquid-permeable and pressure-tight manner, and the secondary reservoir is connected to the at least one feed line and the at least two secondary lines in a liquid-permeable and pressure-tight manner.

In this way, the method benefits from the advantages of the device according to one embodiment.

The remaining device is the device without the two-component cartridge. This alternative therefore relates to devices in which the two-component cartridge is part of the device.

Furthermore, provision can be made for the pressing-out in step B) to take place by axially advancing a first delivery plunger in the main reservoir and a second delivery plunger in the secondary reservoir, wherein in one embodiment the first delivery plunger and the second delivery plunger are advanced in a synchronous manner, and particularly in one embodiment the first delivery plunger and the second delivery plunger are firmly connected to one another and are advanced together in step B).

As a result, the liquids can be driven very easily and the pressure necessary for opening the at least two secondary lines, and optionally the main line, can be exerted by the delivery plungers on the second liquid, and optionally the first liquid.

According to a further development of the method according to one embodiment, the following further steps can be provided:
F) interrupting the pressing-out of the first liquid and of the second liquid;
G) closing the at least two secondary lines by using the restoring force acting from the elastically deformed at least one rubber-elastic body;
H) curing the liquid mixture in the tube and, if present, also in the main line to form a plug;
I) pressing out the first liquid and the second liquid again;
J) expelling the plug through the tube on account of the hydraulic pressure of the first liquid in the main line;
K) opening the at least two secondary lines by an elastic deformation of the at least one rubber-elastic body on account of a force exerted by the second liquid and transmitted hydraulically to the walls of the at least two secondary lines;
L) injecting the second liquid into the first liquid in the main line through the plurality of mutually opposite mouths of the open at least two secondary lines into the main line and thereby mixing the first liquid with the second liquid, wherein the flows of the injected second liquid meet in the main line and, as a result, the mixing of the first liquid with the second liquid is promoted; and
M) pressing out the liquid mixture through the tube connected to the main line.

As a result, the method can be interrupted, but the main line and the secondary line can also be used for producing liquid mixture from the first liquid and the second liquid even after curing.

It is also possible for the main line to be formed in the at least one rubber-elastic body or be formed in a further rubber-elastic body, wherein in step C) the main line is opened by an elastic deformation of the at least one rubber-elastic body or of the further rubber-elastic body on account of a force exerted by the first liquid and hydraulically transmitted to the walls of the main line, and, and in step D) the second liquid is injected into the first liquid into the opened main line through at least one mouth of the open at least two secondary lines into the opened main line.

As a result, the liquid mixture can be pressed through the closing main line into the tube, from where it can be expelled well with a hydraulically transmitted pressure of the first liquid even after curing.

Furthermore, provision can be made that in step G) the main line is closed by the restoring force acting from the elastically deformed at least one rubber-elastic body or by the restoring force acting from the elastically deformed further rubber-elastic body, in step K) the main line is opened by an elastic deformation of the at least one rubber-elastic body or of the further rubber-elastic body on account of a force exerted by the first liquid and hydraulically transmitted to the walls of the main line, and, and in step L) the second liquid is injected into the first liquid into the opened main line through at least one mouth of the open at least two secondary lines into the opened main line.

As a result, the liquid mixture can be pressed through the closing main line into the tube, from where it can be expelled well with a hydraulically transmitted pressure of the first liquid even after curing.

It is provided that there are at least two secondary lines and in step D) the second liquid is injected into the first liquid in the main line through a plurality of mutually opposite mouths of the open at least two secondary lines into the main line, wherein the flows of the injected second liquid meet in the main line and, as a result, the mixing of the first liquid with the second liquid is promoted.

This results in faster and stronger mixing of the first liquid with the second liquid to produce the liquid mixture.

One embodiment is based on the surprising finding that, with at least one elastically closable secondary line for feeding the second liquid into a main line in which the first liquid is conducted, it is possible to mix the two liquids sufficiently well, wherein a plug of the cured liquid mixture can be expelled from the device by using a pressure on the first liquid because the at least one secondary line is elastically closable at the at least one mouth into the main line, such that no undercuts of the plug, which would prevent an expelling of the plug, are formed in the mixing region. The at least one secondary line is hydraulically openable (and thus can be hydraulically opened) by a pressure on the second liquid. One embodiment is also based on the surprising finding that the liquids can be mixed sufficiently with one another even without a static mixer with undercuts when the second liquid is injected laterally into the first liquid in the main line. Due to the fact that the at least one secondary line opens only when a sufficient hydraulic pressure has been built up with the second liquid, it is ensured that the second liquid is injected into the first liquid with a powerful impact. The impact-like introduction of the second liquid into the first liquid that is possible only at high speed produces strong vortices which ensure that the first liquid and the second liquid mix sufficiently strongly in the main line, even without complex structures of static mixers being present for this purpose. For this purpose, the first liquid and the second liquid must not have too high a viscosity. With the rubber-elastic body, which delimits at least the at least one secondary line, and in one embodiment also delimits the main line, it can be ensured that the second liquid is injected with a high pulse into the first liquid due to the necessary minimum pressure.

The device according to one embodiment is constructed in such a way that no mixing spirals are necessary for mixing the liquids. As a result, it is possible to expel a partially or completely cured adhesive in the mixing device and subsequently to further mix and discharge the liquid adhesive components.

The device according to one embodiment and the method according to one embodiment function in such a way that the first liquid is conveyed into the main line. At the same time, the second liquid is pressed from the at least one feed line against the at least one secondary opening of the at least one rubber-elastic body until such a pressure has built up that the at least one secondary line up to the at least one mouth opens and the second liquid is injected through the at least one mouth into the main line. There, the liquid jets of the second liquid meet one another and/or impinge on a wall of the main line and are distributed over the cross section of the main line in the first liquid due to the impact. As a result, the first liquid and the second liquid are mixed with one another.

It is advantageous if the cross section of the main line is as small as possible. When the subsequent pressing of the first liquid and the second liquid ceases, the liquid mixture in the main line can cure in the region of the at least one mouth and in the interior of the tube. After the pressurization of the at least one secondary line by the second liquid ceases, the at least one secondary line closes. When the first and second liquids are pressed out again, the at least one secondary line is opened again by the pressure applied by the second liquid, and the mixed and cured liquid mixture is pressed out of the main line and out of the interior of the tube as a plug or in the form of cured adhesive by the inflowing first liquid. The inflowing second liquid is then mixed again with the injected first liquid in the process.

An exemplary device according to one embodiment may be composed of
  a) a tube having an inner diameter of less than 1.5 mm,
  b) a main feed line which leads to the tube and which is connected or connectable to a main reservoir which contains a first liquid,
  c) a rubber-elastic sleeve as the rubber-elastic body, which contains an axial cavity as the main line, wherein the rubber-elastic sleeve has at least two injection openings as mouths into the cavity, which are designed as secondary lines from the outer lateral surface of the sleeve to the axial cavity of the sleeve, wherein the at least two injection openings are closed in the non-pressurized state,
  d) wherein a proximal end of the tube is inserted into the rubber-elastic sleeve in such a way that the proximal end of the tube does not cover the injection openings,
  e) a casing tube, which coaxially surrounds the rubber-elastic sleeve as a casing, such that a liquid-permeable intermediate space is formed between the outer lateral surface of the sleeve and the inner lateral surface of the casing tube, wherein the intermediate space is connected or connectable to a secondary reservoir containing the second liquid, and
  f) wherein the at least two injection openings of the rubber-elastic sleeve are to be opened by the application of pressure by the second liquid.

The device functions in such a way that the first liquid is conveyed into the main line or into the axial cavity of the sleeve. At the same time, the second liquid is pressed from the at least one feed line against the at least one secondary opening of the at least one rubber-elastic body or in the intermediate space against the sleeve until such a pressure has built up that the at least one secondary line up to the at least one mouth opens or the injection openings open and the second liquid is injected through the at least one mouth or through the injection openings into the main line or the axial cavity. There, the liquid jets of the second liquid meet one another or impinge on a wall of the main line and are distributed over the cross section of the main line or of the axial cavity of the sleeve due to the impact. As a result, the first liquid and the second liquid are mixed with one another.

In this case, it is advantageous if the cross section of the main line or of the axial cavity is as small as possible. When the subsequent pressing of the first liquid and the second liquid ceases, the mixed liquids (the liquid mixture) can cure in the main line or in the axial cavity, in the region of the at least one mouth or the injection nozzles and in the interior of the tube. After the pressurization of the at least one secondary line or the injection openings of the sleeve by the second liquid ceases, the at least one secondary line closes or the injection openings close. When the first liquid and the second liquid are pressed out again, the at least one secondary line or the injection openings is/are opened again by the pressure applied by the second liquid, and the mixed and cured liquids are pressed out of the main line or the cavity of the sleeve and out of the interior of the tube as plugs or in the form of cured adhesive by the inflowing first liquid. The inflowing second liquid is then mixed again with the injected first liquid in the process.

An exemplary method according to one embodiment for producing a liquid mixture can comprise the following steps occurring in succession:
  a) opening a two-component cartridge which has a main reservoir filled with a first liquid, and which has a separate secondary reservoir filled with a second liquid,
  b) connecting the above-mentioned exemplary device to the opened two-component cartridge,
  c) pressing out the two liquids from the main reservoir and the secondary reservoir by axially moving the piston in the direction of a cartridge head of the two-component cartridge,
  d) applying pressure to the rubber-elastic sleeve by the second liquid,
  e) opening the at least two injection openings of the rubber-elastic sleeve by using pressure applied by the second liquid,
  f) flowing of the first liquid into the axial cavity of the sleeve,
  g) injecting the second liquid from the injection openings of the sleeve into the first liquid,
  h) mixing the second liquid with the first liquid in the axial cavity of the sleeve and the interior of the tube, and
  i) pressing out the liquid mixture from the tube by the inflowing first and second liquid. In the exemplary method, provision can be made, after step i), that the pressing-out of the first liquid and the second liquid is ended, and subsequently the following steps are carried out:
  j) curing the mixed liquids in the tube and the axial cavity in the flow direction downstream of the injection nozzles and at the level of the injection nozzles,
  k) pressing out the liquids from the cartridges again,
  l) pressing out the cured liquid mixture with the second liquid from the injection openings,
  m) pressing out the cured liquid mixture with the first liquid through the tube, and n) repeating steps c) to i) and optionally also steps j) to n).

Figure 23:
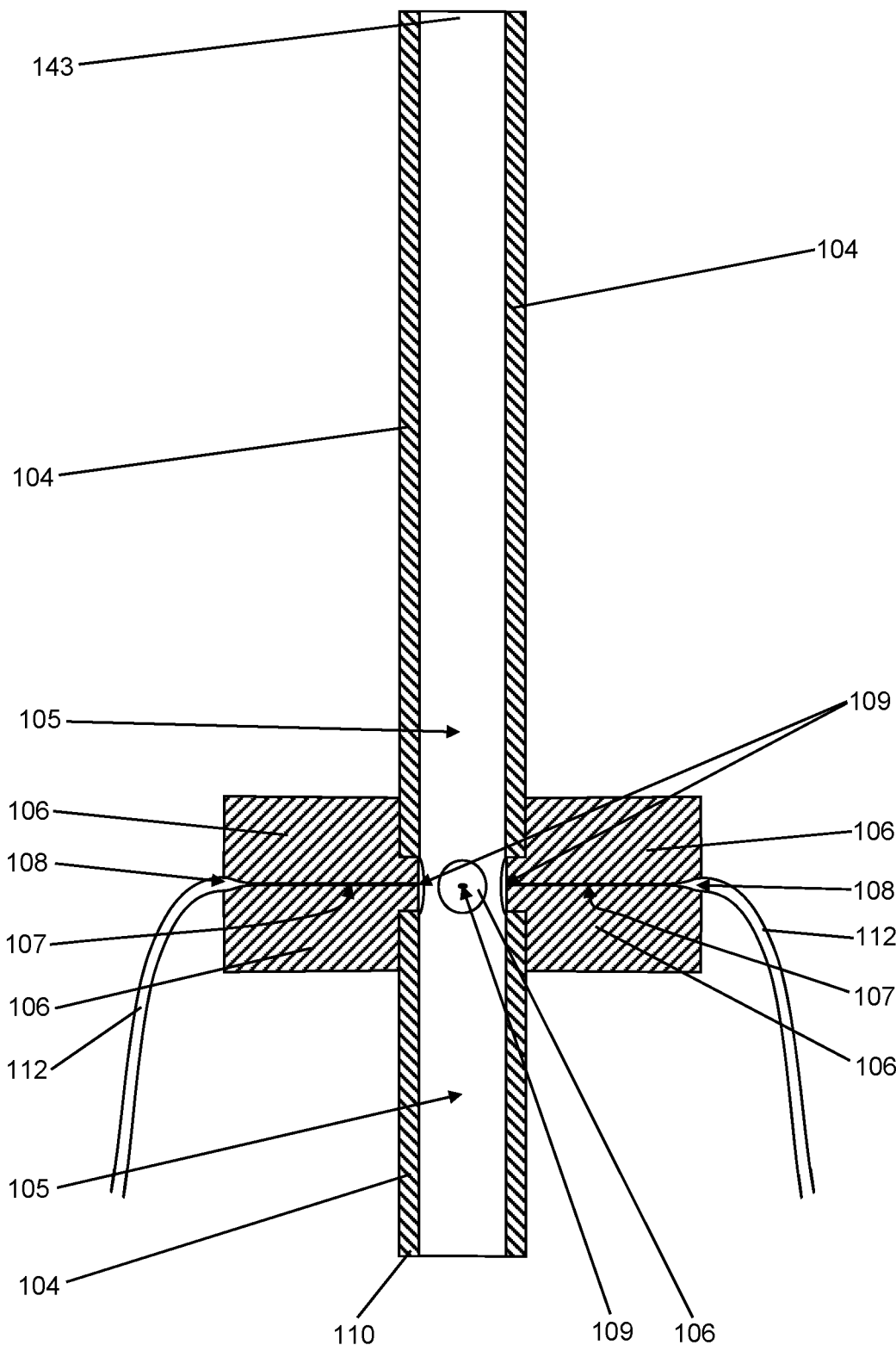
FIG. 23: a schematic cross-sectional view of a further alternative device according to one embodiment with closed secondary lines in a plurality of rubber-elastic bodies.
Figure 24:
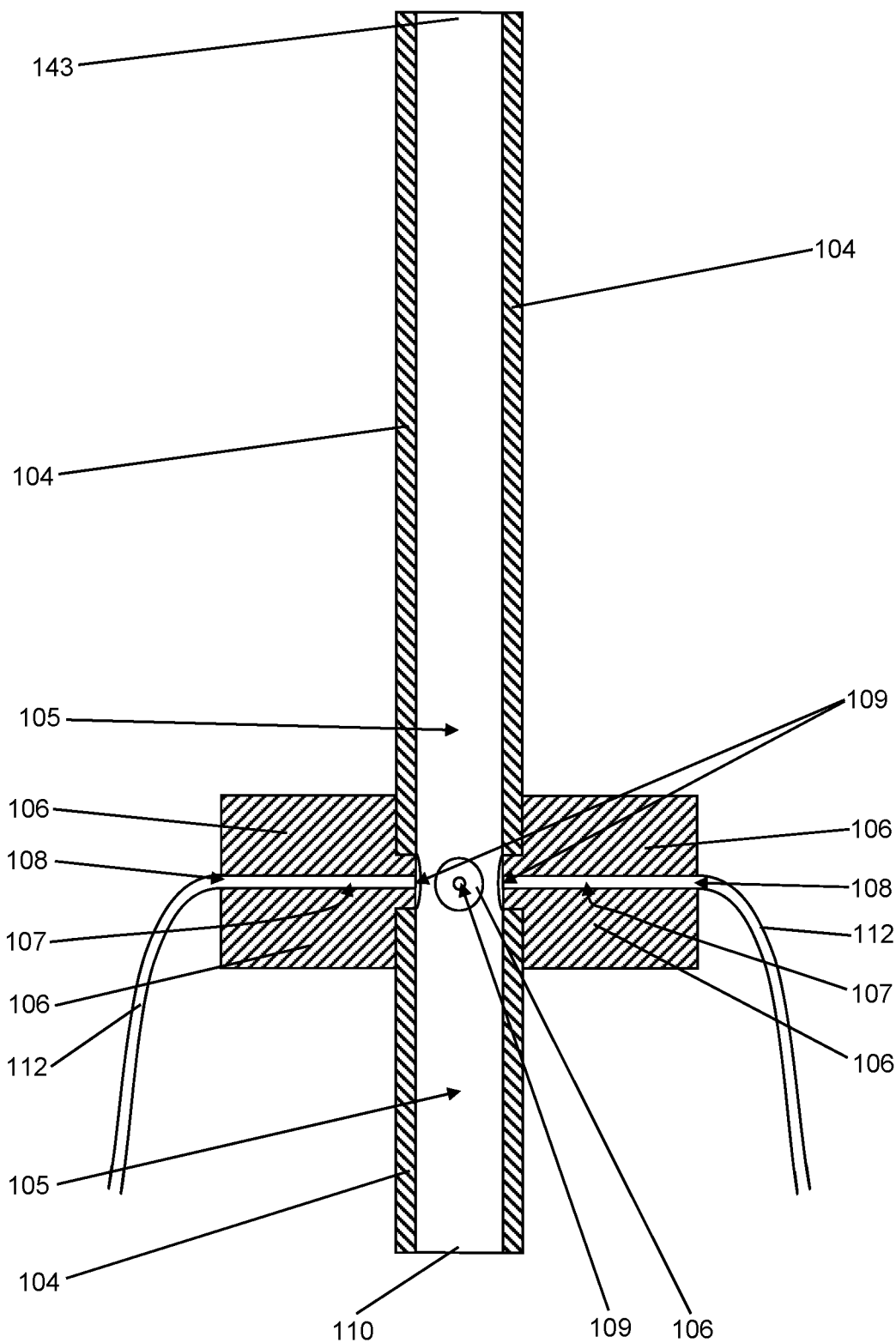
FIG. 24: illustrates a schematic cross-sectional view of the further alternative device of FIG. 23 with opened secondary lines.

FIGS. 1 to 15 show various views of illustrations of a first exemplary embodiment of a device for mixing the liquids and parts thereof. FIGS. 16 to 22 show an alternative second exemplary embodiment of a device. FIGS. 23 and 24 show schematic cross-sectional views of a further alternative third exemplary embodiment.

The first device according to one embodiment according to FIGS. 1 to 15 is provided for mixing a first liquid 1 as main component (represented in FIG. 1 by a honeycomb structure with large honeycombs) and a second liquid 2 as a secondary component (represented in FIG. 1 by a honeycomb structure with medium-sized honeycombs) with one another. In this case, a liquid mixture 3 (represented in FIG. 1 by a honeycomb structure with small honeycombs) is formed which can be discharged through a tube 4, as shown in FIG. 1. The tube 4 in one embodiment consists of a plastic which does not bond to the liquid mixture 3, even if the liquid mixture 3 cures in the tube 4.

The tube 4 can itself be straight and can be connected in a straight line to a main line 5 which is formed in a rubber-elastic body 6. The main line 5 itself is in one embodiment also straight in order to facilitate an expelling of cured liquid mixture 3 from the main line 5 and the tube 4. The rubber-elastic body 6 can consist or be made of an elastomer. Suitable elastomers are, for example, EPDM, silicone rubber, natural rubber, butadiene-acrylonitrile rubber and synthetic polyisoprene rubber. The rubber-elastic body 6 can be designed as a sleeve, wherein the main line 5 can in one embodiment be guided as an axial channel in the interior of the sleeve.

In addition, four secondary lines 7 can be formed in the rubber-elastic body 6 and extend in a straight line radially away from the main line 5 as far as a surface of the rubber-elastic body 6. For this purpose, four secondary openings 8, which lead into the secondary lines 7 and thus into the rubber-elastic body 6, can be arranged in a lateral surface of the sleeve-like rubber-elastic body 6. The secondary openings 8 can be conically shaped or otherwise widened in order to facilitate the pressing of the second liquid 2 into the secondary lines 7 when the secondary lines 7 are closed (see FIGS. 2 and 3).

The secondary lines 7 open into the main line 5 via mouths 9. The secondary lines 7 can be formed by piercing the rubber-elastic body 6. It is essential that the secondary lines 7 are closed in the relaxed state of the rubber-elastic body 6, i.e. without a force or a pressure acting on the line walls of the secondary lines 7 (see FIGS. 2 and 3). In the same way, provision can be made for the main line 5 to be also closed in the relaxed, i.e. pressure-free, state (see FIG. 3).

The mouths 9 can all open into the main line 5 at one location. As a result, liquid jets of the second liquid 2 which are injected into the main line 5 through the mouths 9 meet one another and the kinetic energy of the liquid jets can thus be used to mix the second liquid 2 with the first liquid 1.

The tube 4 can be inserted into the main line 5, with the tube 4 being inserted only so deeply into the main line 5 that it does not cover any of the mouths 9. Theoretically, perforations could also be arranged in the wall of the tube 4 through which the secondary lines 7 open into the main line via the mouths 9.

The first liquid 1 can be pressed into the main line 5 via a main connection 10. For this purpose, the main connection 10 can be connected in a liquid-conducting and pressure-tight manner to the main line 5. A feed line 12 can be provided for feeding the second liquid 2 to the secondary lines 7. The feed line 12 can be connected in a liquid-conducting and pressure-tight manner to the secondary lines 7 via an annular channel surrounding the secondary openings 8 in order to ensure that the second liquid 2 can be injected into the main line 5 through all the secondary lines 7.

Similarly, a main line 14 can be provided which connects the main line 5 from a main opening 16 to the main connection 10. The main opening 16 may be conically shaped or otherwise widened to facilitate pressing of the first liquid 1 into the main line 5 when it is closed (see FIG. 3).

At the end opposite the mouths 8, the feed line 12 can be connected to a secondary connection 18, via which the second liquid 2 can be pressed into the feed line 12. The main connection 10 and the secondary connection 18 can be formed as projecting tubular connecting pieces having a conically tapering end. The connecting pieces can be inserted in or into matching openings of a two-component cartridge.

The main connection 10 and the secondary connection 18 can be designed integrally with an inner part 20. The inner part 20 can consist of a plastic. The feed line 12 and the main feed line 14 can be formed in the interior of the inner part 20. In addition, the inner part 20 can have a cutout for receiving the rubber-elastic body 6, in which the rubber-elastic body 6 is installed. The inner part 20 can be formed rotationally symmetrically on the outside except for the connecting pieces forming the main connection 10 and the secondary connection 18. As a result, the inner part 20 can be rotated against a housing 22 which surrounds the inner part 20. The housing 22 can have projections 24 on its side facing the two-component cartridge, which projections can be connected to an overlapping receptacle 26 on the two-component cartridge in the manner of a bayonet closure. The two-component cartridge can be part of the device according to one embodiment.

The two-component cartridge can have a cartridge head 28 at its front end, which end is provided for connecting to the housing 22, the main connection 10 and the secondary connection 18. Two openings, which are to be connected to the main connection 10 and the secondary connection 18, can be arranged in the cartridge head 28. The two-component cartridge can have two cartridges 30 arranged parallel to one another. The two-component cartridge can consist of plastic except for the two contained liquids 1, 2. Axially displaceable delivery plungers 32, with which the first liquid 1 and the second liquid 2 can be pressed out of the two-component cartridge and into the main feed line 14 and into the feed line 12, can be arranged in the two cartridges 30. The delivery plungers 32 can have a circumferential wiper lip 34 and a circumferential seal 36 in order to be able to expel the first liquid 1 and the second liquid 2 completely out of the cartridges 30. The cartridge 30 for the first liquid 1 can have a larger inner diameter than the cartridge 30 for the second liquid 2. In this way, a mixing ratio can be produced in which a smaller proportion of the second liquid 2 can be admixed with a larger volume of the first liquid 1.

The delivery plungers 32 can be driven from the rear side of the two-component cartridge by using pushrods 38. The cartridges 30 have cylindrical inner spaces in their interior which delimit a main reservoir 40 for the first liquid 1 and a secondary reservoir 42 for the second liquid 2. The first liquid 1 is contained in the main reservoir 40 and the second liquid 2 is contained in the secondary reservoir 42. The main reservoir 40 and the secondary reservoir 42 are delimited at their front side by the cartridge head 28 and at their rear side by the delivery plungers 32, with the contents being able to be pressed by the delivery plungers 32 through the openings in the cartridge head 28 into the main feed line 14 and into the feed line 12.

The finished liquid mixture 3 can be discharged through an open end 43 of the tube 4. The tube 4 is connected at the end opposite the open end 43 to the main line 5, or is inserted into the main line 5.

The two pushrods 38 can be connected to one another at the end opposite the cartridges 30 via a connecting element 44. This ensures that the two delivery plungers 32 can only be advanced synchronously, such that the same mixing ratio of the first liquid 1 and the second liquid 2 is always produced for mixing the liquid mixture 3. The connecting element 44 can also be used as a common handle piece for manually pressing out the first liquid 1 and the second liquid 2 from the two-component cartridge in the manner of a syringe and can be suitably shaped for this purpose. For this purpose, a suitable counter-holder can also be arranged on the rear side of the cartridges 30.

Figure 7:
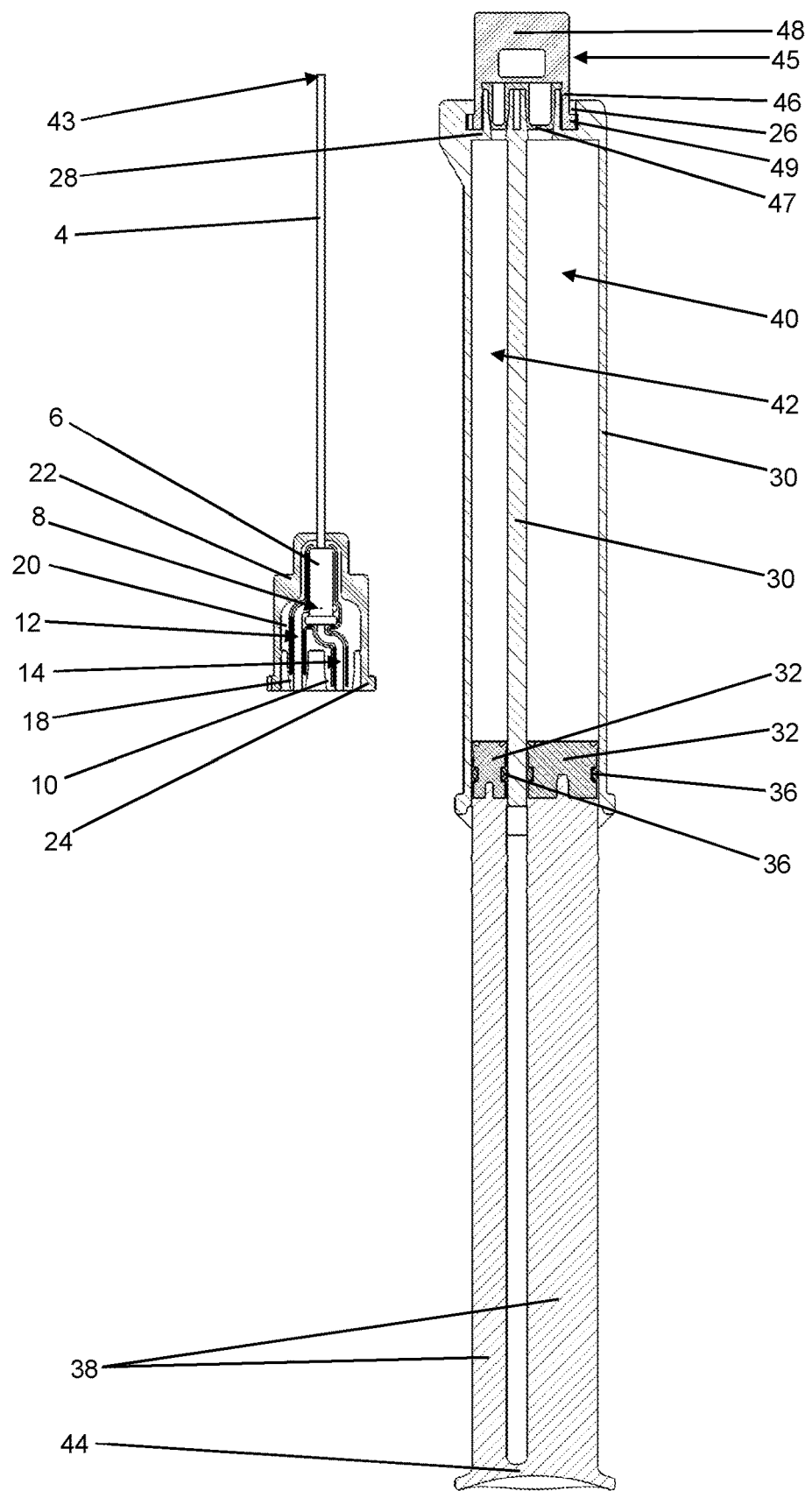
FIG. 7: illustrates a schematic cross-sectional view of the entire device during storage.
Figure 8:
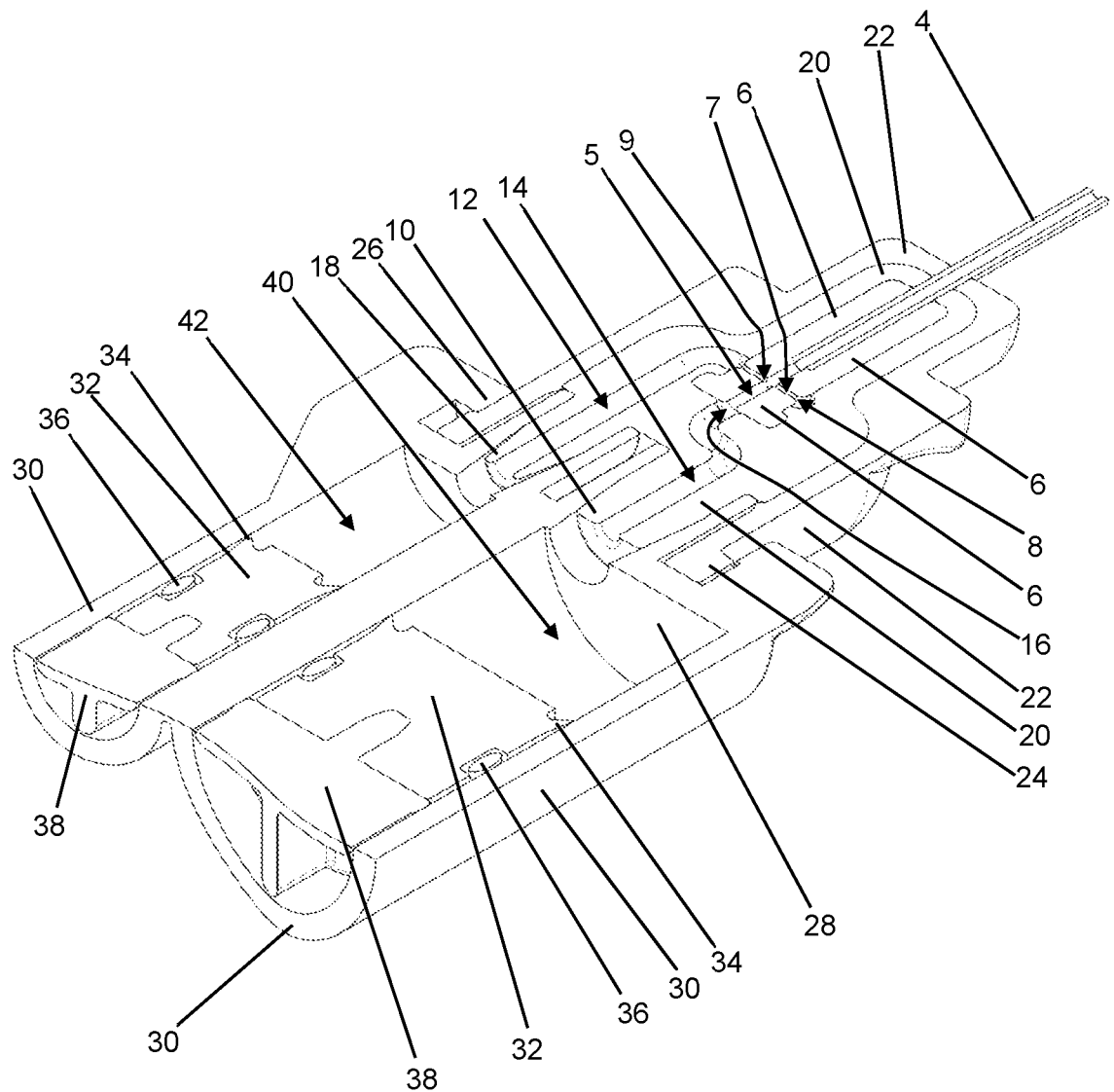
FIG. 8: illustrates a schematic perspective cross-sectional view of a section of the device with opened lines.
Figure 9:
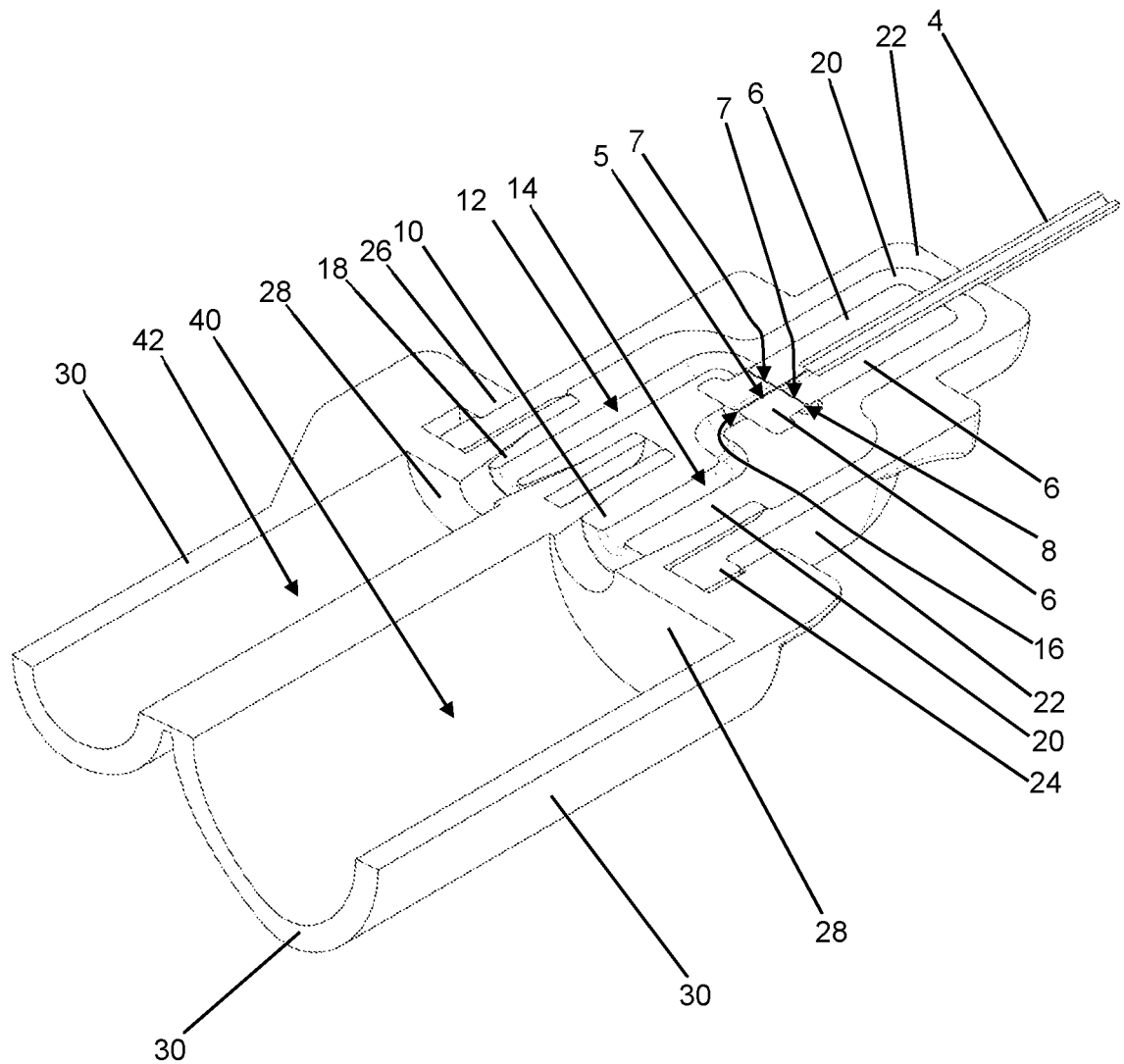
FIG. 9: illustrates a schematic perspective cross-sectional view of a section of the device with closed lines.
Figure 10:
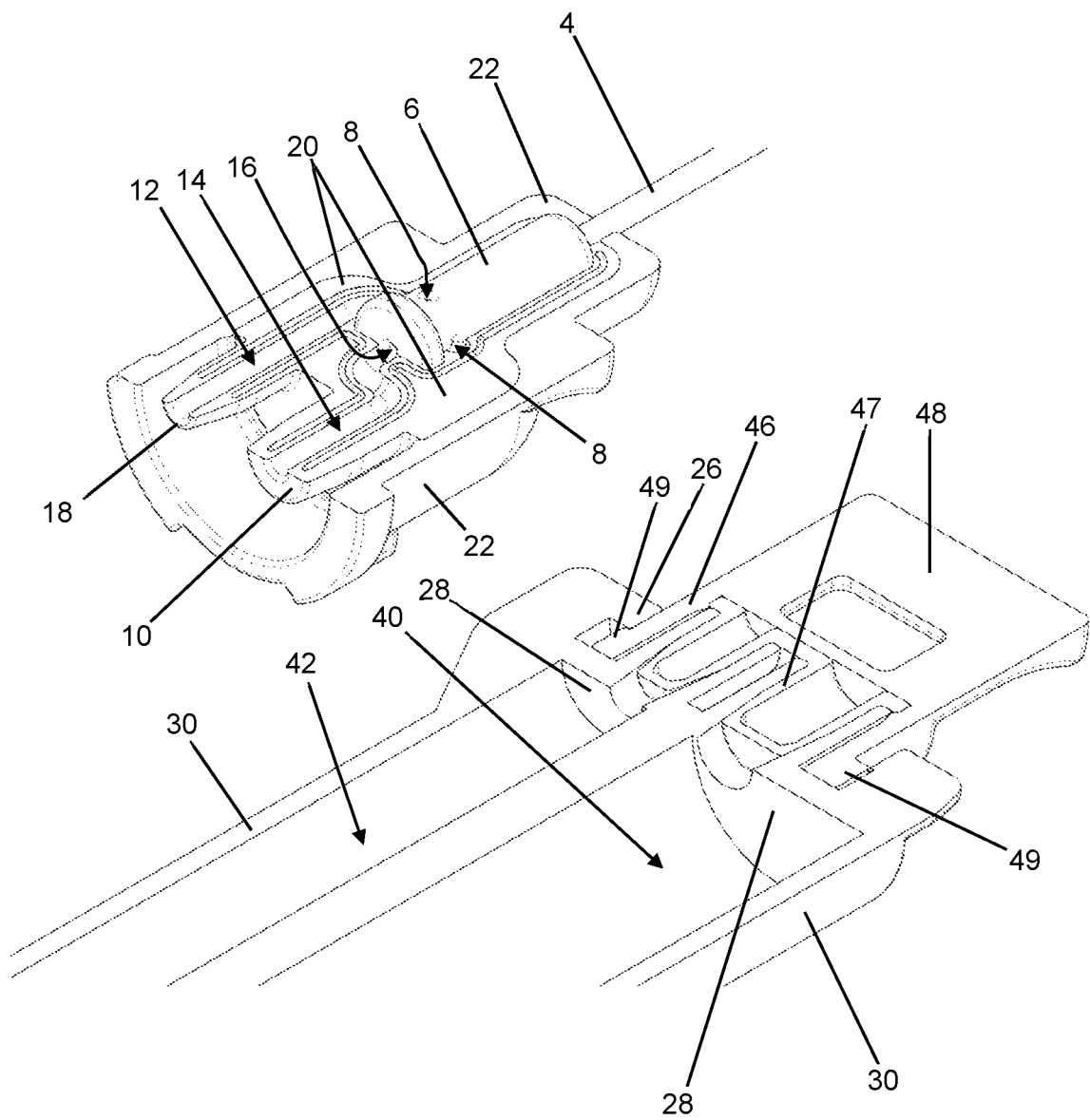
FIG. 10: illustrates a schematic perspective partial cross-sectional view of a section of the device during storage.
Figure 11:
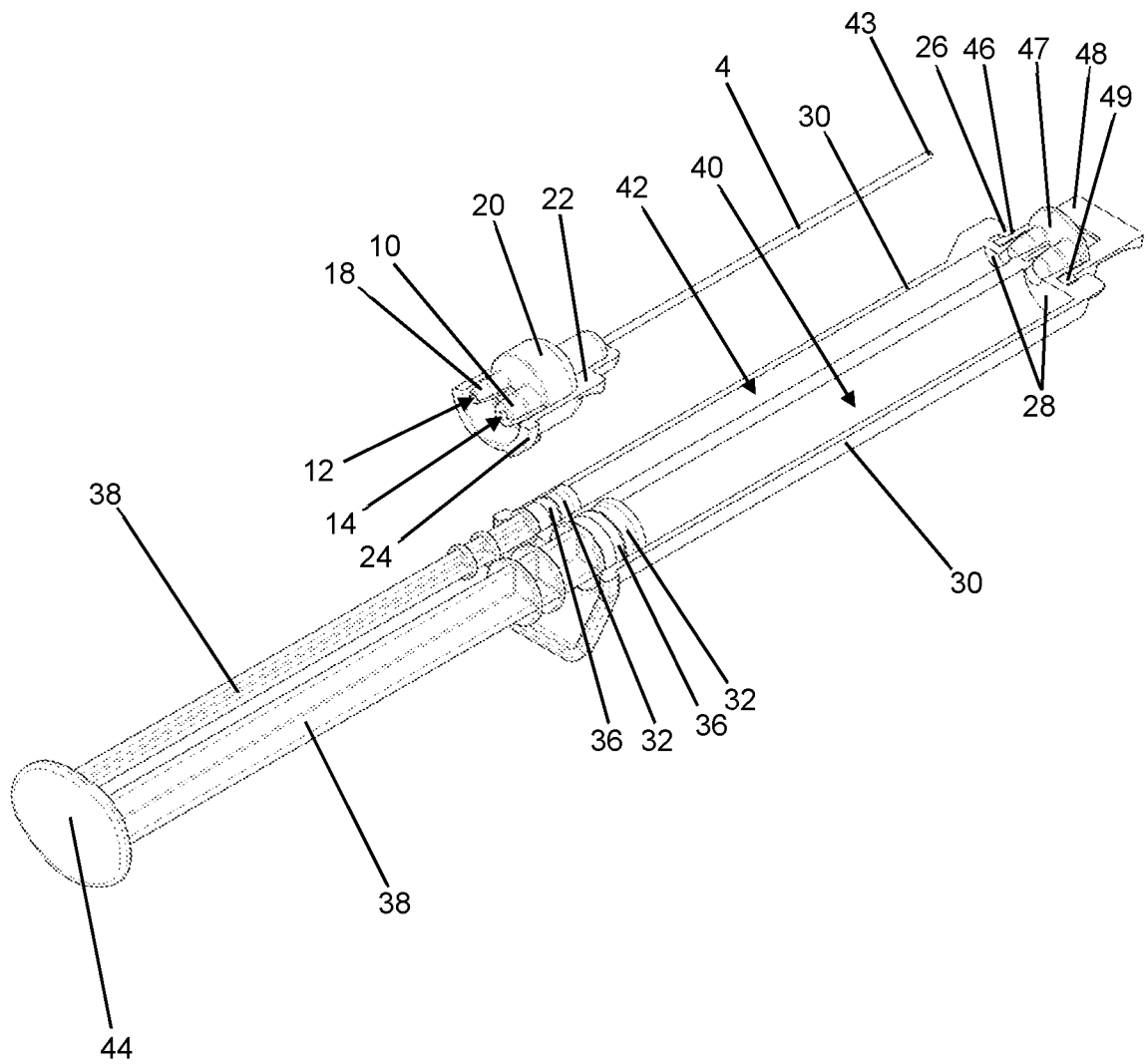
FIG. 11: illustrates a schematic perspective partial cross-sectional view of the device during storage.
Figure 12:
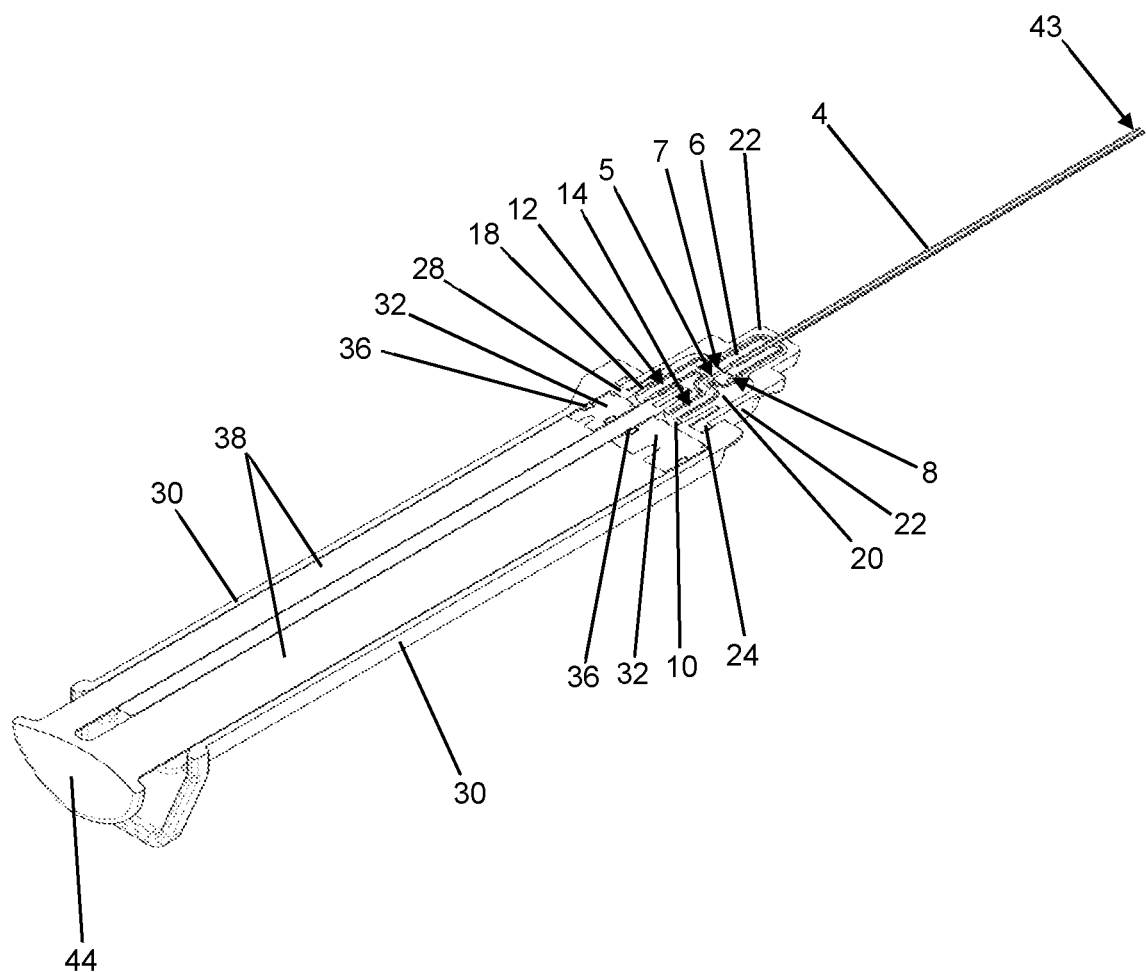
FIG. 12: illustrates a schematic perspective cross-sectional view of the device after the mixing process.
Figure 13:
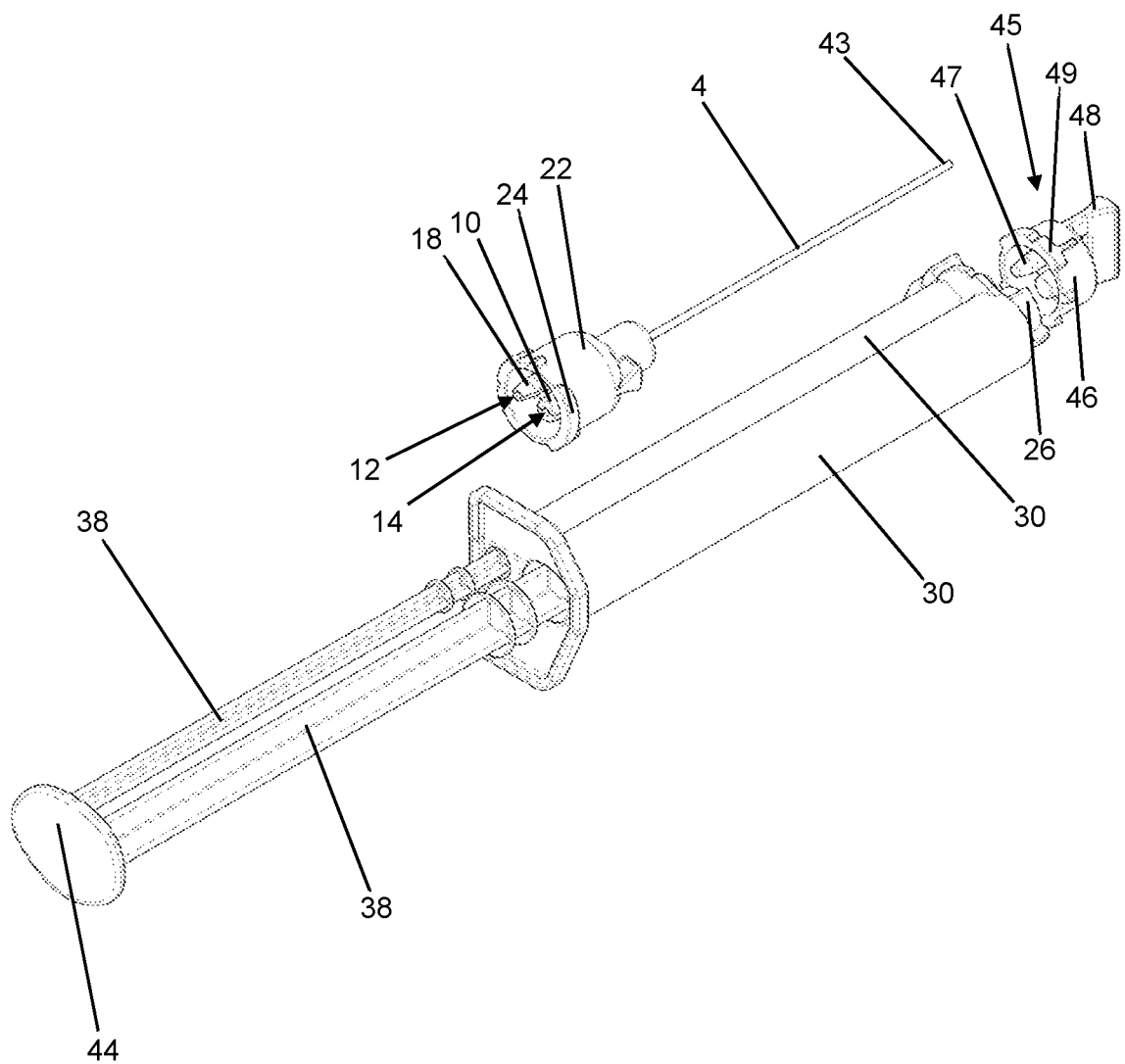
FIG. 13: illustrates a schematic outer perspective view of the device with separated closure.
Figure 14:
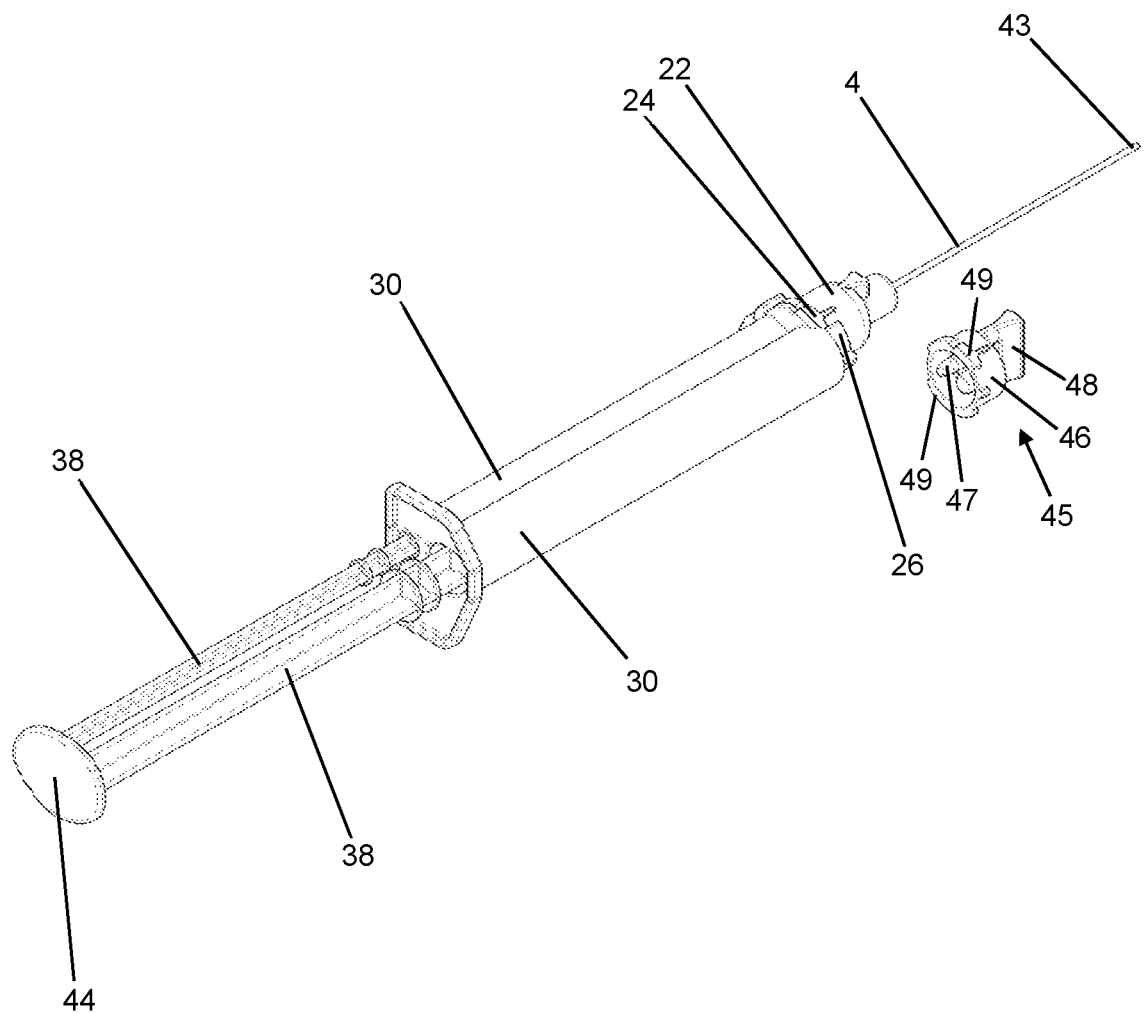
FIG. 14: illustrates a schematic outer perspective view of the device with the mixer connected.
Figure 15:
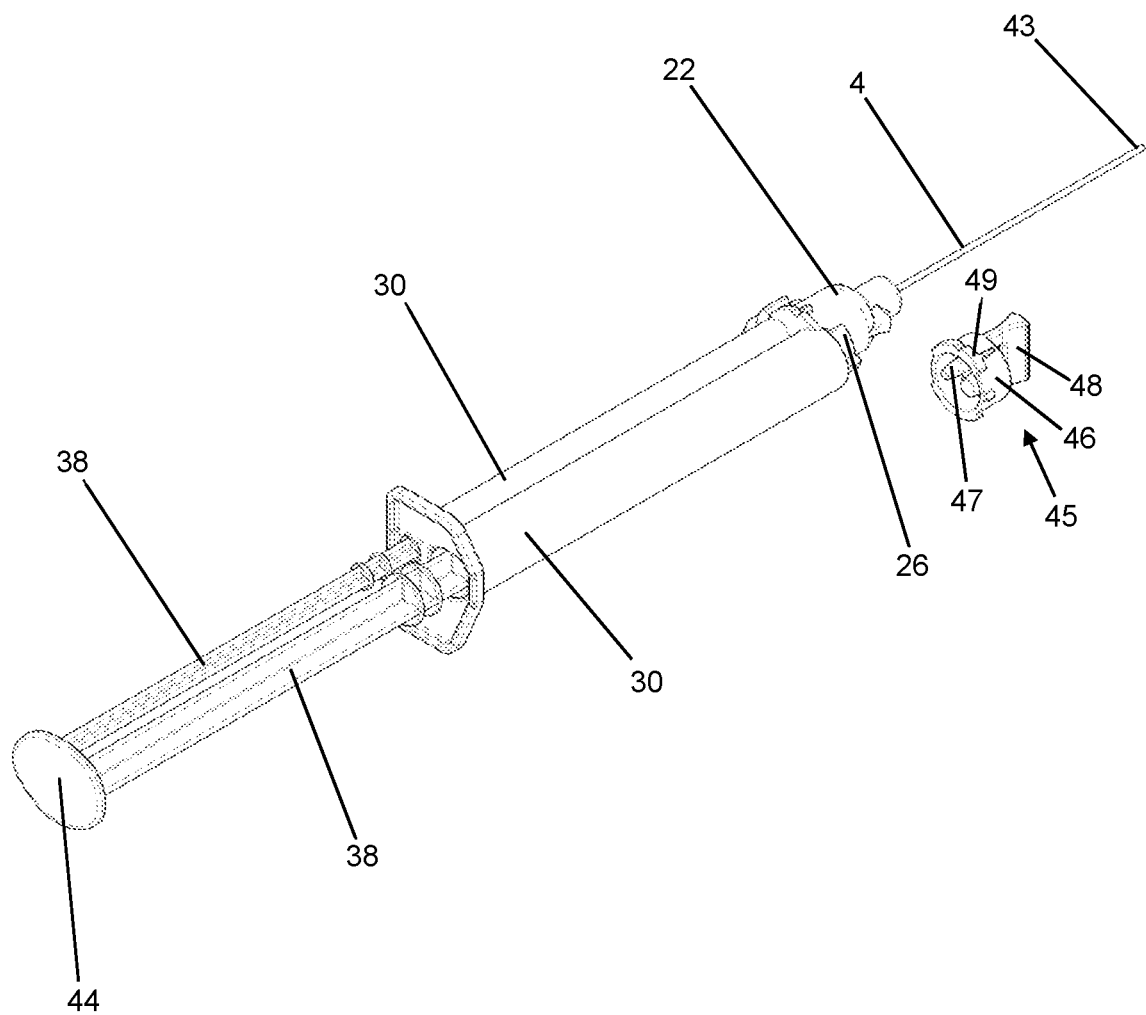
FIG. 15: illustrates a schematic outer perspective view of the device with the mixer attached.

The two-component cartridge can be closed for storage with a closure 45, which closes the two openings in the cartridge head 28 and thus encloses the first liquid 1 and the second liquid 2 in the two-component cartridge (see FIGS. 7, 10 and 11). The closure 45 may have an outer cap 46, an inner part 47 rotatably mounted against the outer cap 46, and a handle 48. Two pins for closing the openings in the cartridge head 28 of the two-component cartridge can be arranged on the inner part 47. The outer cap 46 can have two projections 49, such that the closure 45 can be connected to the outer cap 46 similarly to the housing 22 with the receptacles 26 on the two-component cartridge in the manner of a bayonet closure.

By using the secondary connection 18, the second liquid 2 can be pressed through the feed line 12 into the secondary openings 8 by pressing the second liquid 2 with the delivery plunger 32 out of the secondary reservoir 42 into the feed line 12. Due to the pressure on the second liquid 2, the secondary lines 7 widen on account of an elastic deformation of the rubber-elastic body 6, and the secondary lines 7 become permeable with respect to the second liquid 2. Finally, the mouths 9 also open into the main line 5 and the second liquid 2 is injected under pressure into the first liquid 1 conducted in the main line 5. Because of the kinetic energy with which the second liquid 2 is injected and the fact that the liquid flows of the second liquid 2 meet, a strong mixing of the first liquid 1 and the second liquid 2 is brought about to form the liquid mixture 3.

In the same way as the secondary lines 7 are openable by a pressure on the second liquid 2, the main line 5 can also be opened by a pressure on the first liquid 1 and widened against the elastic force of the rubber-elastic body 6.

When the discharge of the first liquid 1 and the second liquid 2 is interrupted because no more pressure is exerted on the delivery plungers 32, the secondary lines 7 and optionally also the main line 5 are closed again on account of the elastic force stored in the rubber-elastic body 6. In this case, the mouths 9 into the main line 5 are also closed. The first liquid 1, the second liquid 2 and the liquid mixture 3 are pressed into the open tube 4 from the main line 5 and the secondary lines 7. In the tube 4 and optionally in the main line 5, the liquid mixture 3 can cure and form a plug. At a later point in time, the plug can be expelled hydraulically by a pressure on the first liquid 1, and the device is immediately ready for use again to produce a new uncured liquid mixture 3.

FIGS. 16 to 22 show various views of illustrations of a second exemplary embodiment of an alternative device according to one embodiment for mixing the liquids and parts thereof.

Figure 22:
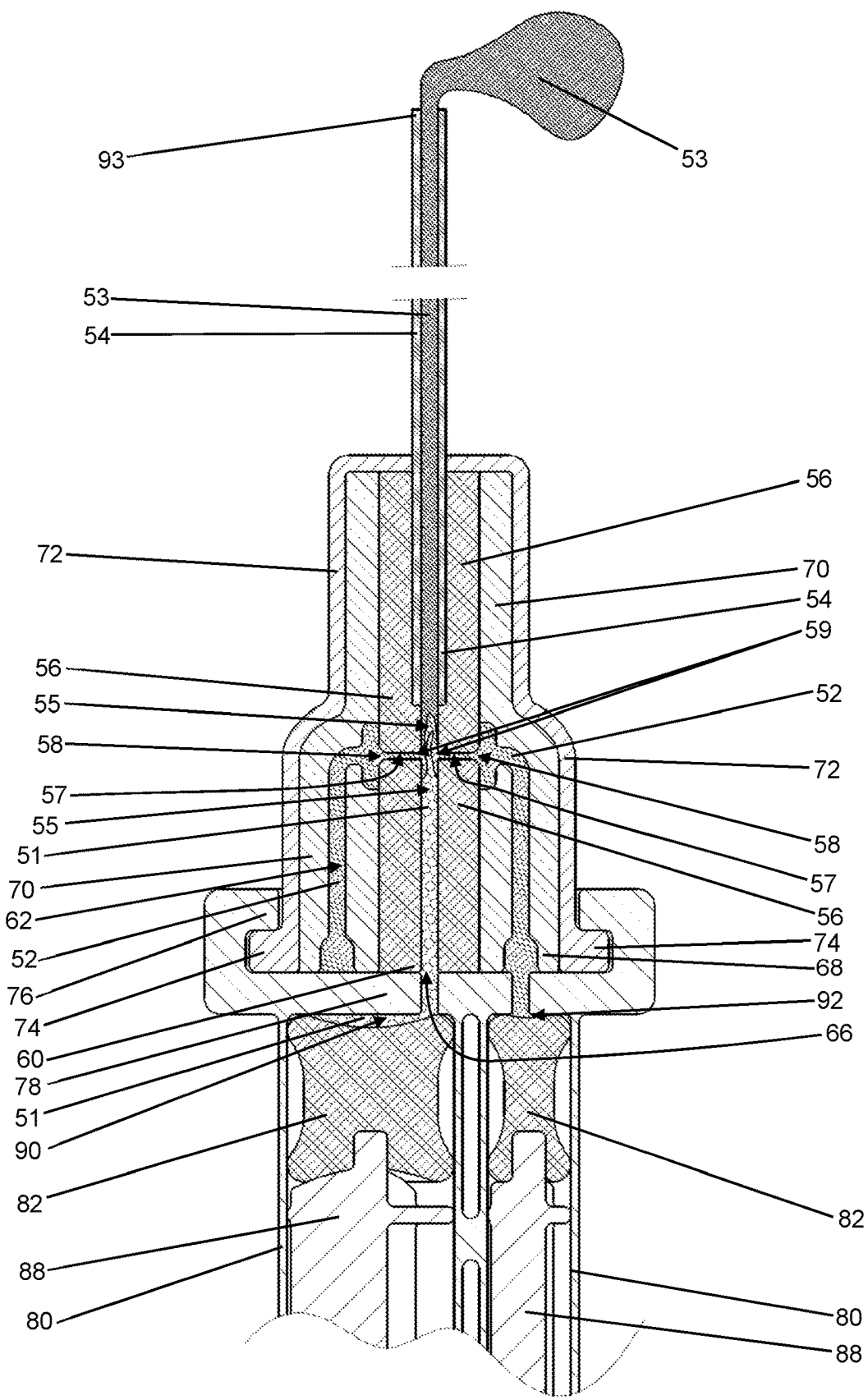
FIG. 22: illustrates a detail enlargement in the form of a schematic cross-sectional view of the alternative device of FIGS. 16 to 21 at the end of the mixing process.

The second alternative device according to one embodiment according to FIGS. 16 to 22 is provided for mixing a first liquid 51 as main component (represented in FIG. 22 by a honeycomb structure with large honeycombs) and a second liquid 52 as secondary component (represented in FIG. 22 by a honeycomb structure with medium-sized honeycombs) with one another. In this case, a liquid mixture 53 (represented in FIG. 22 by a honeycomb structure with small honeycombs) is formed which can be discharged through a tube 54, as shown in FIG. 22. The tube 54 in one embodiment consists of a plastic which does not bond to the liquid mixture 53, even if the liquid mixture 53 cures in the tube 54.

The tube 54 can itself be straight and can be connected in a straight line to a main line 55 which is formed in a rubber-elastic body 56. The main line 55 itself is in one embodiment also straight in order to facilitate an expelling of cured liquid mixture 53 from the main line 55 and the tube 54. The rubber-elastic body 56 can consist or be made of an elastomer. Suitable elastomers are, for example, EPDM, silicone rubber, natural rubber, butadiene-acrylonitrile rubber and synthetic polyisoprene rubber. The rubber-elastic body 56 can be designed as a sleeve, wherein the main line 55 can in one embodiment be guided as an axial channel in the interior of the sleeve.

In addition, four secondary lines 57 can be formed in the rubber-elastic body 56 and extend in a straight line radially away from the main line 55 as far as a surface of the rubber-elastic body 56. For this purpose, four secondary openings 58, which lead into the secondary lines 57 and thus into the rubber-elastic body 56, can be arranged in a lateral surface of the sleeve-like rubber-elastic body 56. The secondary openings 58 can be conically shaped or otherwise widened in order to facilitate the pressing of the second liquid 52 into the secondary lines 57 when the secondary lines 57 are closed (see FIGS. 18 and 22).

The secondary lines 57 open into the main line 55 via mouths 59. The secondary lines 57 can be formed by piercing the rubber-elastic body 56. It is essential that the secondary lines 57 are closed in the relaxed state of the rubber-elastic body 56, i.e. without a force or a pressure acting on the line walls of the secondary lines 57. In the same way, provision can be made for the main line 55 to be also closed in the relaxed, i.e. pressure-free, state. However, it is also possible for the main line 55 to not be closable.

The mouths 59 can all open into the main line 55 at one location. As a result, liquid jets of the second liquid 52 which are injected into the main line 55 through the mouths 59 meet one another and the kinetic energy of the liquid jets can thus be used to mix the second liquid 52 with the first liquid 51.

The tube 54 can be inserted into the main line 55, with the tube 54 being inserted only so deeply into the main line 55 that it does not cover any of the mouths 59. Theoretically, perforations could also be arranged in the wall of the tube 54 through which the secondary lines 57 open into the main line via the mouths 59.

The first liquid 51 can be pressed into the main line 55 via a main connection 60. In this embodiment, the main connection 60 forms the end of the main line 55 opposite the tube 54. A plurality of feed lines 62 can be provided for feeding the second liquid 52 to the secondary lines 57. The feed lines 62 can be connected to the secondary lines 57 in a liquid-conducting and pressure-tight manner via an annular channel surrounding the secondary openings 58 in order to ensure that the second liquid 52 can be injected through all the secondary lines 57 into the main line 55, irrespective of the feed lines 62 via which the second liquid 52 is pressed in. Alternatively, the feed lines 62 can also be connected to one another in other ways in order to ensure that the second liquid 52 can be pressed into the rubber-elastic body 56 in each of the secondary openings 58.

A main opening 66 can open at the main connection 60 into the main line 55. The main line 66 may be conically shaped or otherwise widened to facilitate pressing of the first liquid 51 into the main line 55 when it is closed.

The feed lines 62 can be connected at the ends opposite the mouths 58 to a secondary connection 68 in each case via which the second liquid 52 can be pressed into the feed lines 62. The main connection 60 and the secondary connection 68 can be designed as a flange in a flat sealing surface. The flange can be attached to a matching mating flange of a two-component cartridge.

The main connection 60 and the secondary connection 68 can be designed integrally with an inner part 70. The inner part 70 can consist of a plastic. The feed lines 62 can be formed in the interior of the inner part 70. In addition, the inner part 70 can have a cutout in the form of a central continuous passage for receiving the rubber-elastic body 56, in which the rubber-elastic body 56 is installed. The inner part 70 can be formed rotationally symmetrically on the outside. As a result, the inner part 70 can be rotated against a housing 72 which surrounds the inner part 70. The housing 72 can have projections 74 on its side facing the two-component cartridge, which projections can be connected to an overlapping receptacle 76 on the two-component cartridge in the manner of a bayonet closure. The two-component cartridge can be part of the device according to one embodiment.

The two-component cartridge can have a cartridge head 78 at its front end, which is provided for connecting at the flange of the inner part 70 to the rubber-elastic body 56, for connecting the main connection 60 and the secondary connection 68. Two openings, which are to be connected to the main connection 60 and the secondary connection 68, can be arranged in the cartridge head 78. The two-component cartridge can have two cartridges 80 arranged parallel to one another. The two-component cartridge can consist of plastic except for the two contained liquids 51, 52. Axially displaceable delivery plungers 82, with which the first liquid 51 and the second liquid 52 can be pressed out of the two-component cartridge and into the main line 55 and into the feed line 62, can be arranged in the two cartridges 80. The cartridge 80 for the first liquid 51 may have a larger inner diameter than the cartridge 80 for the second liquid 52. In this way, a mixing ratio can be produced in which a smaller proportion of the second liquid 52 can be admixed with a larger volume of the first liquid 51.

The delivery plungers 82 can be driven from the rear side of the two-component cartridge by using pushrods 88. The cartridges 80 have cylindrical inner spaces in their interior which delimit a main reservoir 90 for the first liquid 51 and a secondary reservoir 92 for the second liquid 52. The first liquid 51 is contained in the main reservoir 90 and the second liquid 52 is contained in the secondary reservoir 92. The main reservoir 90 and the secondary reservoir 92 are delimited at their front side by the cartridge head 78 and at their rear side by the delivery plungers 82, with the contents being able to be pressed by the delivery plungers 82 through the openings in the cartridge head 78 into the main line 55 and into the feed line 62.

The finished liquid mixture 53 may be discharged through an open end 93 of the tube 54. The tube 54 is connected at the end opposite the open end 93 to the main line 55, or is inserted into the main line 5.

The two pushrods 88 can be connected to one another at the end opposite the cartridges 80 via a connecting element 94. This ensures that the two delivery plungers 82 can only be advanced synchronously, such that the same mixing ratio of the first liquid 51 and the second liquid 52 is always produced for mixing the liquid mixture 53. The connecting element 94 can also be used as a common handle piece for manually pressing out the first liquid 51 and the second liquid 52 from the two-component cartridge in the manner of a syringe and can be suitably shaped for this purpose. For this purpose, a suitable counter-holder can also be arranged on the rear side of the cartridges 80.

Figure 16:
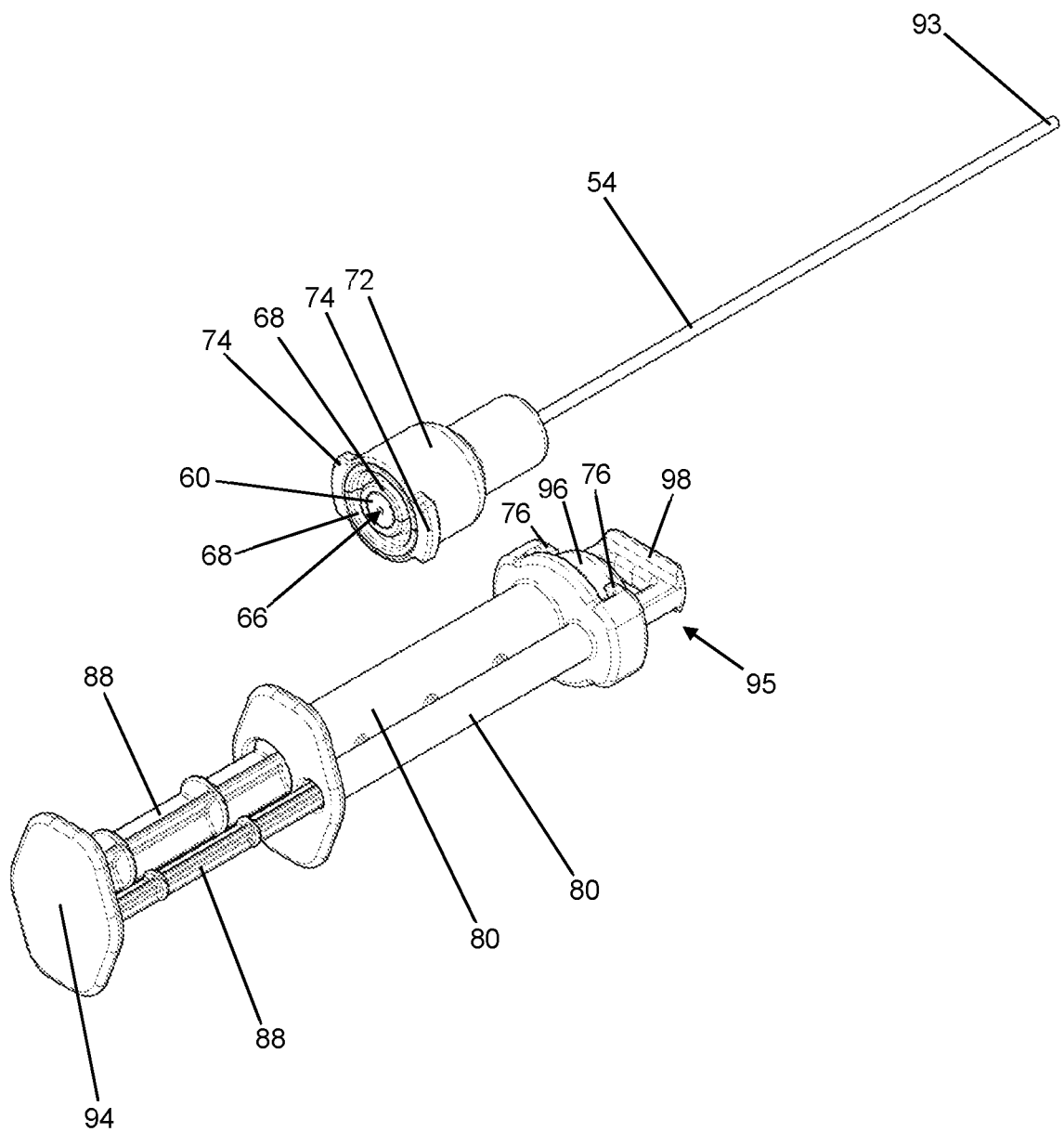
FIG. 16: illustrates a schematic outer perspective view of an alternative device according to one embodiment during storage.
Figure 17:
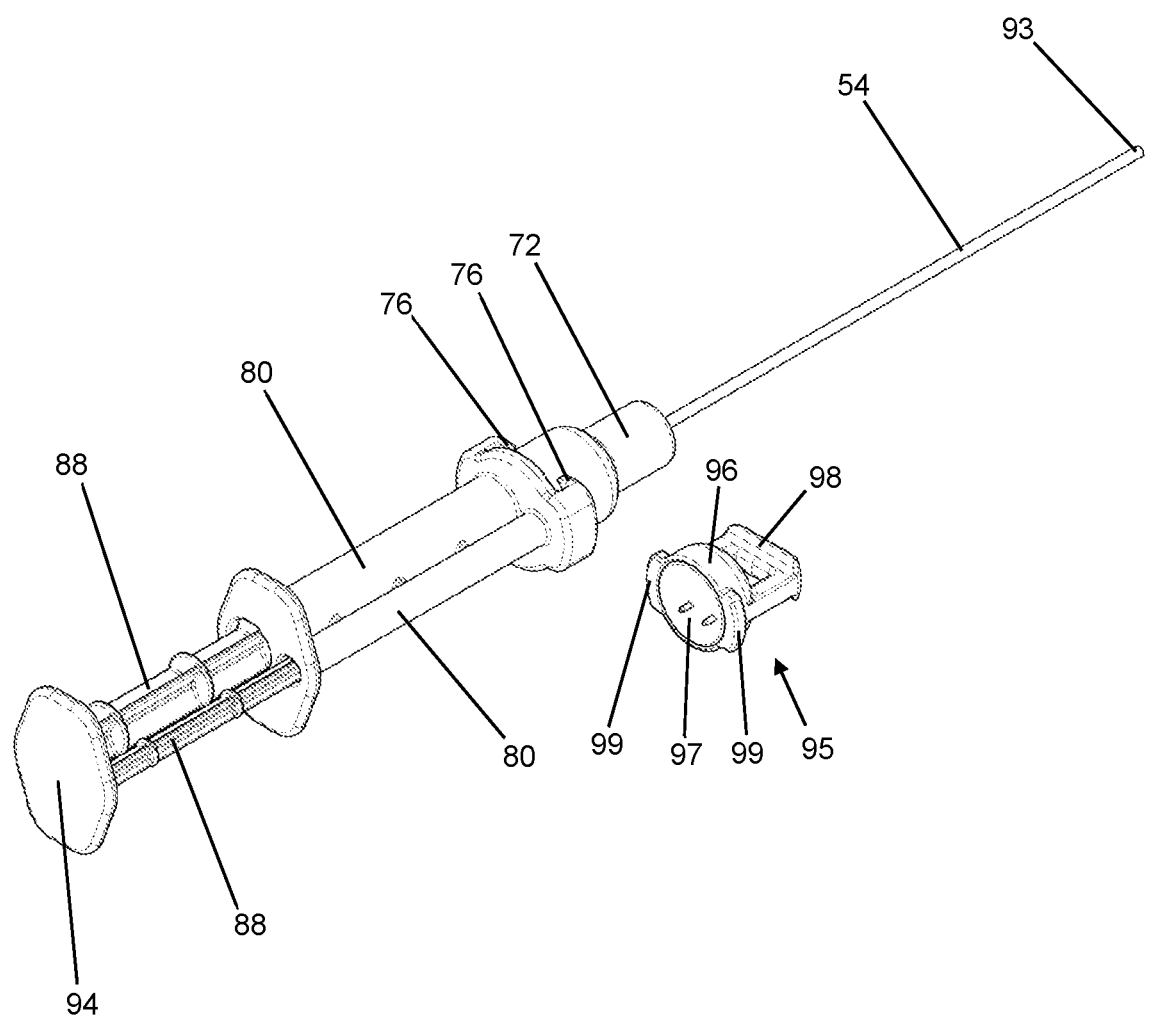
FIG. 17: illustrates a schematic outer perspective view of the alternative device of FIG. 16 ready for mixing.
Figure 18:
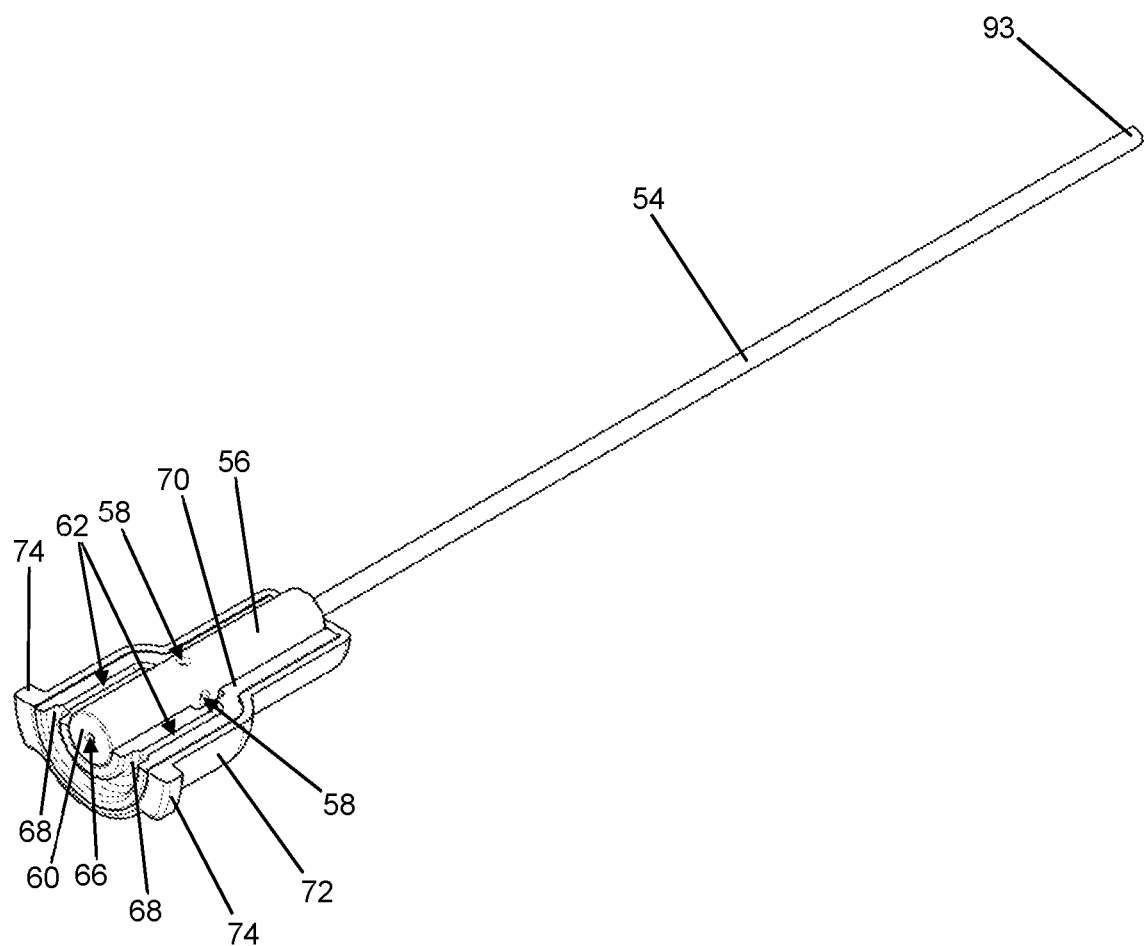
FIG. 18: illustrates a schematic perspective partial cross-sectional view of a part of the alternative device of FIGS. 16 and 17.
Figure 19:
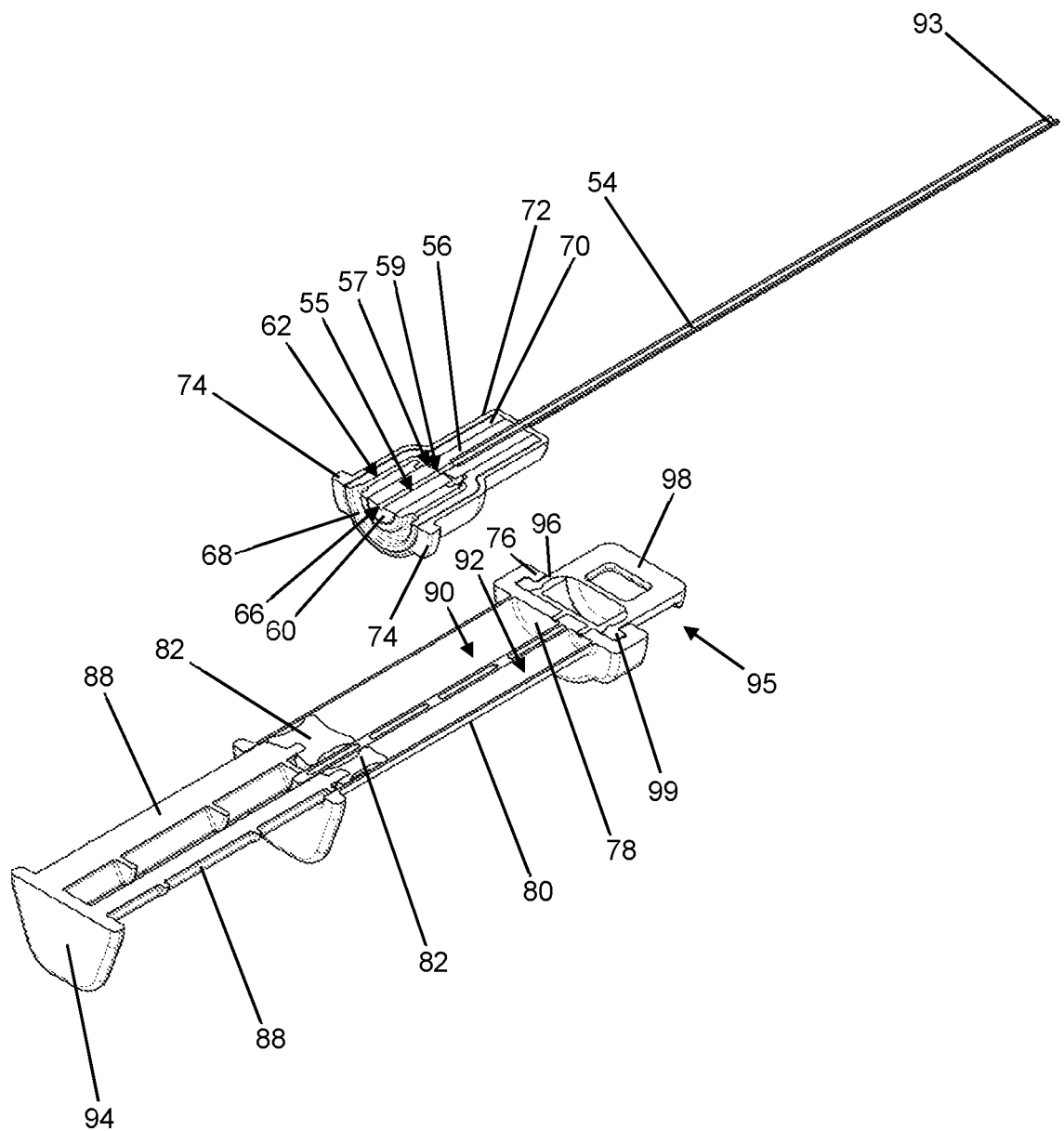
FIG. 19: illustrates a schematic perspective cross-sectional view of the alternative device of FIG. 16.
Figure 20:
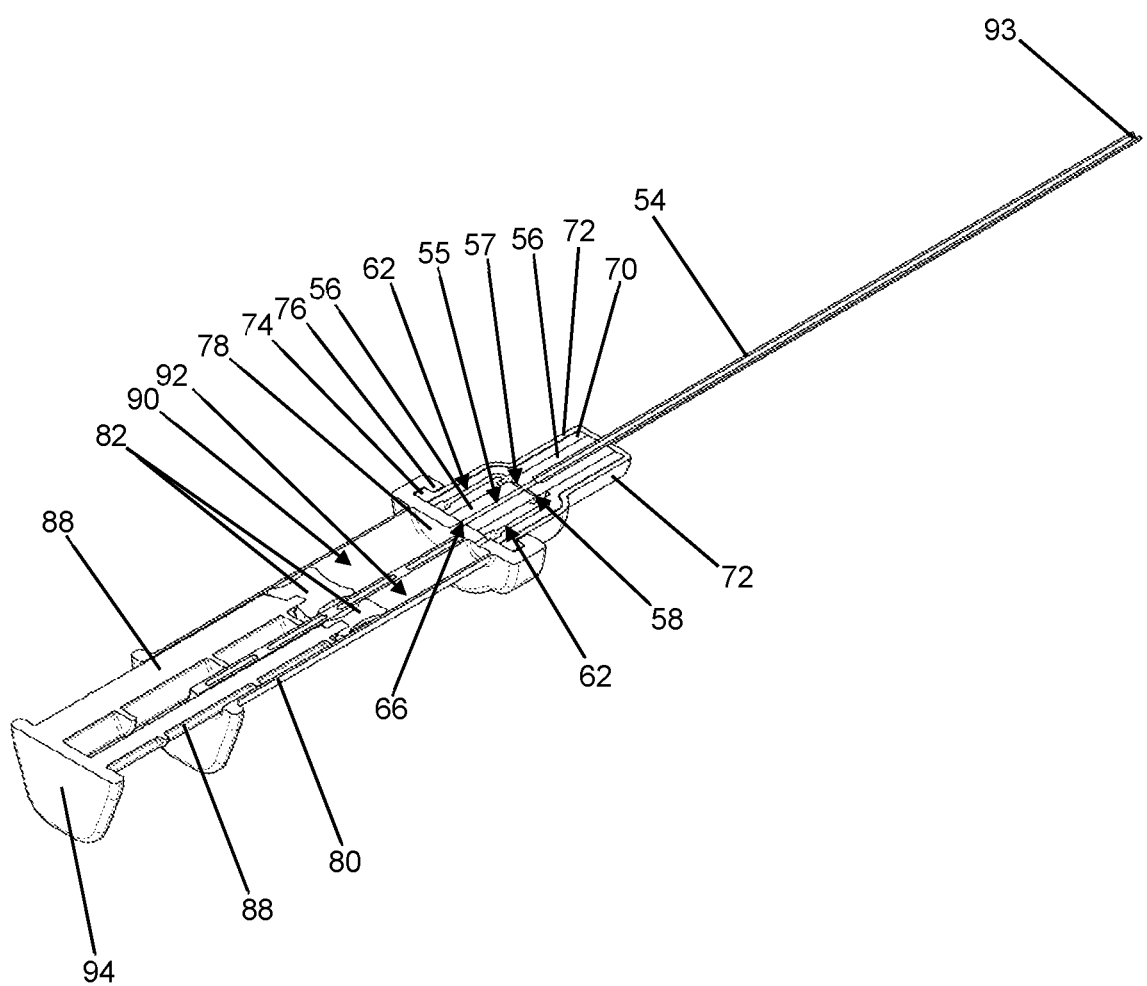
FIG. 20: illustrates a schematic perspective cross-sectional view of the alternative device of FIGS. 16 to 19 during mixing.
Figure 21:
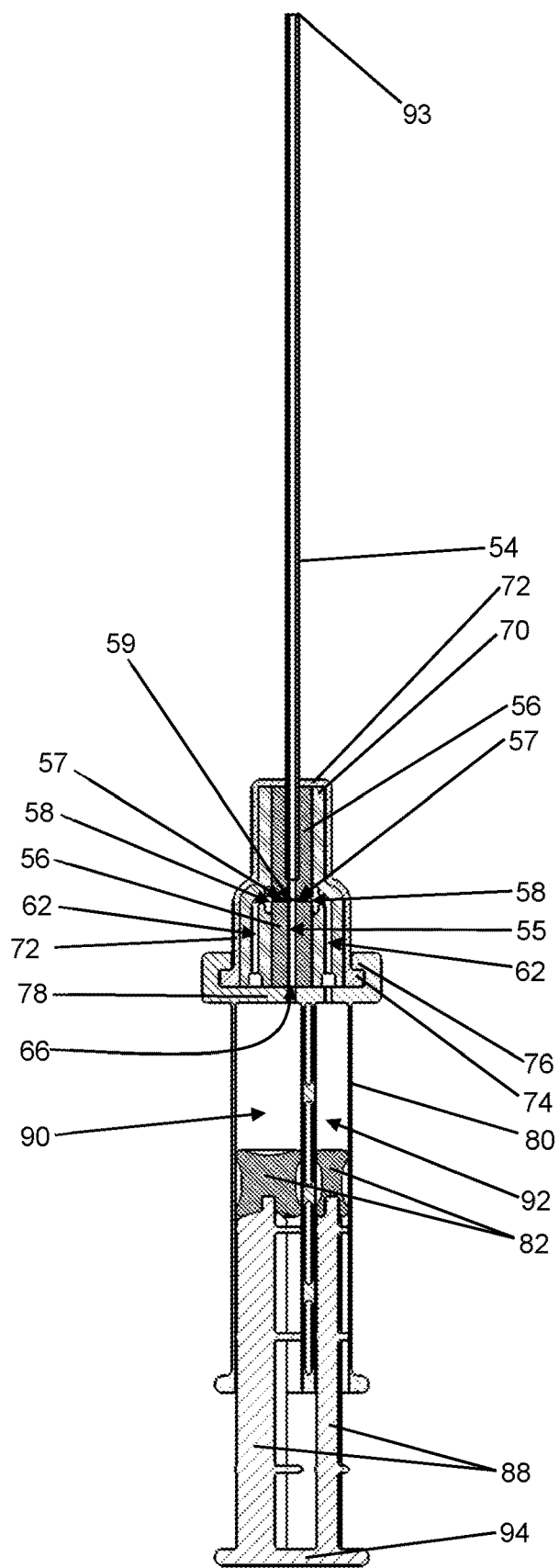
FIG. 21: illustrates a schematic cross-sectional view of the alternative device of FIGS. 16 to 20 during mixing.

The two-component cartridge can be closed for storage with a closure 95, which closes the two openings in the cartridge head 78 and thus encloses the first liquid 51 and the second liquid 52 in the two-component cartridge (see FIGS. 16 and 19). The closure 95 may have an outer cap 96, an inner part 97 rotatably mounted against the outer cap 96, and a handle 98. Two pins for closing the openings in the cartridge head 78 of the two-component cartridge can be arranged on the inner part 97. The outer cap 96 can have two projections 99, such that the closure 95 can be connected to the outer cap 96 similarly to the housing 72 with the receptacles 76 on the two-component cartridge in the manner of a bayonet closure.

By using the secondary connection 68, the second liquid 52 can be pressed through the feed line 62 into the secondary openings 58 by pressing the second liquid 52 with the delivery plunger 82 out of the secondary reservoir 92 into the feed line 62. Owing to the pressure on the second liquid 52, the secondary lines 57 widen on account of an elastic deformation of the rubber-elastic body 56, and the secondary lines 57 become permeable with respect to the second liquid 52. Finally, the mouths 59 also open into the main line 55 and the second liquid 52 is injected under pressure into the first liquid 51 conducted in the main line 55. Because of the kinetic energy with which the second liquid 52 is injected and the fact that the liquid flows of the second liquid 52 meet, a strong mixing of the first liquid 51 and the second liquid 52 is brought about to form the liquid mixture 53.

In the same way as the secondary lines 57 are openable by a pressure on the second liquid 52, the main line 55 can also theoretically be opened by a pressure on the first liquid 51 and widened against the elastic force of the rubber-elastic body 56.

When the discharge of the first liquid 51 and the second liquid 52 is interrupted because no more pressure is exerted on the delivery plungers 82, the secondary lines 57 are closed again on account of the elastic force stored in the rubber-elastic body 56. In this case, the mouths 59 into the main line 55 are also closed. The first liquid 51, the second liquid 52 and the liquid mixture 53 are pressed into the open tube 54 from the secondary lines 57. In the tube 54 and in the main line 55, the liquid mixture 53 can cure and form a plug. At a later point in time, the plug can be expelled hydraulically by a pressure on the first liquid 51, and the device is immediately ready for use again to produce a new uncured liquid mixture 53.

FIGS. 23 to 24 show various views of illustrations of a third exemplary embodiment of a further alternative device according to one embodiment for mixing the liquids and parts thereof.

The third alternative device according to one embodiment according to FIGS. 23 and 24 is provided for mixing a first liquid and a second liquid with one another. This produces a liquid mixture which can be discharged through a tube 104. The tube 104 in one embodiment consists of a plastic which does not bond to the liquid mixture, even if the liquid mixture cures in the tube 104.

The tube 104 may itself be straight and delimit a main line 105 in its interior. Four rubber-elastic bodies 106 may be applied to the tube 104 which delimit the main line 105 in the region of openings in the tube 104, in one embodiment such that the walls of the main line 105 which are formed by the rubber-elastic bodies 106 are flush with the inner wall of the tube 104. The main line 105 itself is in one embodiment straight to facilitate an expelling of cured liquid mixture from the main line 105 and the tube 104. The rubber-elastic bodies 106 can consist or be made of an elastomer. Suitable elastomers are, for example, EPDM, silicone rubber, natural rubber, butadiene-acrylonitrile rubber and synthetic polyisoprene rubber. The rubber-elastic bodies 106 can be designed as a sleeve, wherein a secondary line 107 can in one embodiment be guided as an axial channel in each case in the interior of the sleeve.

A secondary line 107 can be formed in each case in each of the rubber-elastic bodies 106, which extends in a straight line radially away from the main line 105 as far as a surface of the rubber-elastic bodies 106. For this purpose, a secondary opening 108, which leads into the secondary lines 107 and thus into the rubber-elastic bodies 106, can be arranged in each case in a main surface of the sleeve-like rubber-elastic bodies 106. The secondary openings 108 can be widened in order to facilitate the pressing of the second liquid into the secondary lines 107 when the secondary lines 107 are closed (see FIG. 23).

The secondary lines 107 open into the main line 105 via mouths 109. The mouths 109 are arranged in the surfaces of the rubber-elastic bodies 106 which delimit the main line 105. The secondary lines 107 can be formed by axially piercing the rubber-elastic bodies 106. It is essential that the secondary lines 107 are closed in the relaxed state of the rubber-elastic bodies 106, i.e. without a force or a pressure acting on the line walls of the secondary lines 107.

The mouths 109 can all open into the main line 105 at one location. As a result, liquid jets of the second liquid which are injected into the main line 105 through the mouths 109 meet one another and the kinetic energy of the liquid jets can thus be used to mix the second liquid with the first liquid. The mouths in the tube 104 are arranged in such a way that they leave openings 109 open.

The first liquid can be pressed into the main line 105 via a main connection 110. A plurality of feed lines 112 can be provided for feeding the second liquid to the secondary lines 107. The feed lines 112 can be connected in a liquid-conducting and pressure-tight manner to the secondary lines 107 in order to ensure that the second liquid can be injected into the main line 105. The feed lines 112 can be connected to one another to ensure that the second liquid can be pressed into the rubber-elastic bodies 106 in each of the secondary openings 108. The feed lines 112 can consist of a solid plastic. In addition, the feed lines 112 can be inserted into the secondary lines 107 in order to widen the secondary lines 107 in the region of the secondary openings 108 and to produce a tight connection.

The feed lines 112 can be connected at the ends opposite the mouths 108 to a secondary connection in each case via which the second liquid can be pressed into the feed lines 112. The main connection 110 and the secondary connection can be attached to a two-component cartridge (not shown, but similar to the first or second exemplary embodiment).

The finished liquid mixture may be discharged through an open end 143 of the tube 104. The distal part of the tube 104 with the open end 143 is connected to the proximal part of the tube 104 that substantially delimits the main line 105. In other words, in this embodiment, the main line 105 is substantially delimited by a (proximal) tube 104 which is connected in a liquid-conducting and pressure-tight manner to the (distal part) tube 104 and is designed integrally with the (distal part) tube 104. Therefore, in this embodiment, the main line 105 is also connected to the tube 104 (the distal part) in a liquid-permeable manner on the side opposite the open end 143.

By the secondary connection, the second liquid can be pressed through the feed line 112 into the secondary openings 108. Owing to the pressure on the second liquid, the secondary lines 107 widen on account of an elastic deformation of the rubber-elastic bodies 106, and the secondary lines 107 become permeable with respect to the second liquid. Finally, the mouths 109 also open into the main line 105 (see FIG. 24), and the second liquid is injected under pressure into the first liquid guided in the main line 105. Because of the kinetic energy with which the second liquid is injected and the fact that the liquid flows of the second liquid meet, a strong mixing of the first liquid and the second liquid is brought about to form the liquid mixture.

When the discharge of the first liquid and the second liquid is interrupted, the secondary lines 107 will close again on account of the elastic force stored in the rubber-elastic bodies 106. In this case, the mouths 109 into the main line 105 are also closed. The second liquid and the liquid mixture are pressed out of the secondary lines 107 in this case into the open tube 104. The liquid mixture can cure and form a plug in the tube 104 and in the main line 105. The plug can be hydraulically pressed out of the main line 105 at a later point in time by a pressure on the first liquid, and the device is immediately ready for use again to produce a new uncured liquid mixture.

The features of the invention disclosed in the above description, as well as in the claims, figures and exemplary embodiments, may be essential both individually and in any combination for realizing the invention in its various embodiment forms.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

The invention claimed is:

1. A device for mixing small volumes of a first liquid and a second liquid, the device comprising:
   a tube having a line cross-sectional area of at most 2 mm$^2$ or having an inner diameter of at most 1.5 mm, wherein the tube has an open end;
   a main line connected to the tube in a liquid-permeable manner on a side opposite the open end;

at least one rubber-elastic body, which delimits a line wall of the main line at least in some regions or which delimits the entire main line;

at least one secondary line, which is formed in the at least one rubber-elastic body, wherein the at least one secondary line extends from at least one secondary opening in a surface of the at least one rubber-elastic body up to the main line and opens into the main line via at least one mouth in the at least one rubber-elastic body;

a main connection for introducing the first liquid into the main line; and at least one feed line for introducing the second liquid into the at least one secondary line, wherein the at least one feed line is connected to the at least one secondary opening in a liquid-permeable manner;

wherein the at least one secondary line is closed in the at least one rubber-elastic body without the action of a force and is hydraulically openable by a pressure being exerted on the second liquid, supplied to the at least one secondary line, by an elastic deformation of the at least one rubber-elastic body; and wherein an open at least one secondary line closes without the pressure being exerted on the supplied second liquid by the force of the elastically deformed at least one rubber-elastic body.

2. The device according to claim 1, wherein the at least one rubber-elastic body is a single rubber-elastic body in which the main line and the at least one secondary line are formed.

3. The device according to claim 2, wherein the tube is inserted into the main line, and wherein the tube does not cover the at least one mouth of the at least one secondary line into the main line.

4. The device according to claim 2, wherein the at least one rubber-elastic body is covered by a casing at least in the region of a secondary opening, wherein the casing coaxially surrounds the at least one rubber-elastic body, and the main line runs along or parallel to the axis of the casing in the at least one rubber-elastic body, and wherein the at least one feed line is designed as at least one liquid-permeable intermediate space between the casing and the at least one rubber-elastic body.

5. The device according to claim 1, wherein the tube is connected to the main line in a liquid-tight and pressure-tight manner, the main connection is connected to the main line in a liquid-tight manner and also in a pressure-tight manner, and the second feed line is connected to the at least one secondary opening in a liquid-tight and also pressure-tight manner.

6. The device according to claim 1, wherein an inner diameter of the main line or the inner diameter of the main line in an expanded state has the same internal cross section as the tube, or the tube in the interior thereof delimits a straight cylindrical line, wherein no projections or depressions are in the tube, and the tube is smooth in the interior thereof.

7. The device according to claim 6, wherein the at least one mouth is flush with an inner wall of the main line or the tube is flush with the main line or the tube is flush with the main line in the expanded state.

8. The device according to claim 1, wherein the at least one secondary line is at least 5 mm long, or the main line is at least 5 mm long.

9. The device according to claim 1, wherein the main line is connected via the main connection to a main reservoir containing the first liquid, and the at least one feed line is connected to a secondary reservoir containing the second liquid, wherein a first delivery plunger is arranged in the main reservoir, such that the first liquid is pressable by the first delivery plunger from the main reservoir into the main line, and a second delivery plunger is arranged in the secondary reservoir, such that the second liquid is pressable by the second delivery plunger from the secondary reservoir into the at least one feed line, and wherein the first delivery plunger and the second delivery plunger are firmly connected to one another.

10. The device according to claim 9, wherein the first liquid and the second liquid are starting components of a medical tissue adhesive, and the device is a device for producing a medical tissue adhesive.

11. The device according to claim 1, wherein the tube has a line cross-sectional area of at most 1 mm$^2$ or the inner diameter of the tube is at most 0.5 mm.

12. The device according to claim 1, wherein the at least one mouth or the at least one secondary line in an opened state has a diameter of at most 0.3 mm.

13. The device according to claim 1, wherein the at least one secondary line is at least two secondary lines and the at least one mouth is at least two mouths, wherein the at least two mouths are arranged on opposite sides of the main line, such that the second liquid injected into the main line through the at least two mouths directly meets in the main line.

14. The device according to claim 1, wherein the main line and the at least one feed line are connected to a two-component cartridge, wherein the main line is connected via the main connection to a first chamber of the two-component cartridge, and the at least one feed line is connected to a second chamber of the two-component cartridge, wherein the first liquid is contained as a first starting component in the first cartridge and the second liquid is contained as a second starting component in the second cartridge.

15. The device according to claim 1, wherein the main line is formed in the at least one rubber-elastic body or is formed in a further rubber-elastic body, wherein the main line is closed in the at least one rubber-elastic body or in the further rubber-elastic body without the action of the force and is hydraulically openable by a pressure being exerted on the first liquid supplied to the main line by elastic deformation of the at least one rubber-elastic body or of the further rubber-elastic body, and wherein an open main line closes without a pressure being exerted on the supplied first liquid by the force of the elastically deformed at least one rubber-elastic body.

16. The device according to claim 1, wherein the at least one mouth into the at least one rubber-elastic body is funnel-shaped and provides an opening into the at least one rubber-elastic body, even when no pressure acts on the at least one rubber-elastic body.

17. A method for producing a mixture of two liquids, the method comprising the following chronological steps:

A) providing a two-component cartridge having a main reservoir, in which a first liquid is contained, and a secondary reservoir, in which a second liquid is contained;

B) pressing out the first liquid from the main reservoir into a main line and pressing out the second liquid from the secondary reservoir into at least two secondary lines, wherein the at least two secondary lines are closed and formed in at least one rubber-elastic body;

C) opening the at least two secondary lines by elastic deformation of the at least one rubber-elastic body on account of a force exerted by the second liquid and transmitted hydraulically to walls of the at least one secondary line;

D) injecting the second liquid into the first liquid in the main line through a plurality of mutually opposite mouths of the opened at least two secondary lines into the main line, wherein the at least two mouths are arranged on opposite sides of the main line, such that the second liquid injected into the main line through the at least two mouths directly meets in the main line, thereby mixing the first liquid with the second liquid, wherein the flows of the injected second liquid meet in the main line and, as a result, the mixing of the first liquid with the second liquid is promoted; and E) pressing out the first and second liquid mixture through a tube connected to the main line.

18. The method according to claim 17, wherein the method is carried out with a device for mixing small volumes of the first liquid and the second liquid, the device comprising:

wherein the tube has a line cross-sectional area of at most 2 mm$^2$ or has an inner diameter of at most 1.5 mm, wherein the tube has an open end;

wherein the main line is connected to the tube in a liquid-permeable manner on a side opposite the open end;

wherein the at least one rubber-elastic body delimits a line wall of the main line at least in some regions or which delimits the entire main line;

wherein the at least one secondary line is formed in the at least one rubber-elastic body, wherein the at least one secondary line extends from at least one secondary opening in a surface of the at least one rubber-elastic body up to the main line and opens into the main line via at least one mouth in the at least one rubber-elastic body;

a main connection for introducing the first liquid into the main line; and at least one feed line for introducing the second liquid into the at least one secondary line, wherein the at least one feed line is connected to the at least one secondary opening in a liquid-permeable manner;

wherein the at least one secondary line is closed in the at least one rubber-elastic body without the action of the force and is hydraulically openable by a pressure being exerted on the second liquid, supplied to the at least one secondary line, by an elastic deformation of the at least one rubber-elastic body; and wherein an open at least one secondary line closes without the pressure being exerted on the supplied second liquid by the force of the elastically deformed at least one rubber-elastic body.

19. The method according to claim 18, wherein the main reservoir is connected in a liquid-permeable and pressure-tight manner to the main connection and the main line, and the secondary reservoir is connected to the at least one feed line and the at least two secondary lines in a liquid-permeable and pressure-tight manner, or after step A) and before step B) a step A2) is carried out:

A2) connecting the device to the two-component cartridge, wherein the main reservoir is connected to the main connection and the main line in a liquid-permeable and pressure-tight manner, and the secondary reservoir is connected to the at least one feed line and the at least two secondary lines in a liquid-permeable and pressure-tight manner.

20. The method according to claim 17, wherein the pressing-out in step B) takes place by axially advancing a first delivery plunger in the main reservoir and a second delivery plunger in the secondary reservoir, wherein the first delivery plunger and the second delivery plunger are advanced in a synchronous manner, and the first delivery plunger and the second delivery plunger are firmly connected to one another and are advanced together in step B).

21. The method according to claim 17 further comprising:

F) interrupting the pressing-out of the first liquid and of the second liquid;

G) closing the at least two secondary lines by means of the force acting from the elastically deformed at least one rubber-elastic body;

H) curing the liquid mixture in the tube and, if present, also in the main line to form a plug;

I) pressing out the first liquid and the second liquid again;

J) expelling the plug through the tube on account of the hydraulic pressure of the first liquid in the main line;

K) opening the at least two secondary lines by an elastic deformation of the at least one rubber-elastic body on account of a force exerted by the second liquid and transmitted hydraulically to walls of the at least two secondary lines;

L) injecting the second liquid into the first liquid in the main line through the plurality of mutually opposite mouths of the open at least two secondary lines into the main line and thereby mixing the first liquid with the second liquid, wherein the flows of the injected second liquid meet in the main line and, as a result, the mixing of the first liquid with the second liquid is promoted; and M) pressing out the liquid mixture through the tube connected to the main line.

22. The method according to claim 21, wherein the main line is formed in the at least one rubber-elastic body or is formed in a further rubber-elastic body, wherein in step C) the main line is opened by an elastic deformation of the at least one rubber-elastic body or of the further rubber-elastic body on account of the force exerted by the first liquid and transmitted hydraulically to walls of the main line, and in step D) the second liquid is injected into the first liquid into the opened main line through at least one mouth of the open at least two secondary lines into the opened main line.

23. The method according to claim 21, wherein in step G) the main line is closed by the force acting from the elastically deformed at least one rubber-elastic body or by the force acting from the elastically deformed further rubber-elastic body, in step K) the main line is opened by an elastic deformation of the at least one rubber-elastic body or of the further rubber-elastic body on account of the force exerted by the first liquid and hydraulically transmitted to walls of the main line, and in step L) the second liquid is injected into the first liquid into the opened main line through at least one mouth of the open at least two secondary lines into the opened main line.

* * * * *